United States Patent

Naya et al.

[11] Patent Number: 6,140,338
[45] Date of Patent: Oct. 31, 2000

[54] CHEMOKINE RECEPTOR ANTAGONISTS

[75] Inventors: Akira Naya; Yufu Owada; Toshihiko Saeki; Kenji Ohwaki; Yoshikazu Iwasawa, all of Tsukuba, Japan

[73] Assignee: Banyu Pharmaceutical, Co., Ltd., Tokyo, Japan

[21] Appl. No.: 09/147,595

[22] PCT Filed: Jul. 23, 1997

[86] PCT No.: PCT/JP97/02548

§ 371 Date: Jan. 29, 1999

§ 102(e) Date: Jan. 29, 1999

[87] PCT Pub. No.: WO98/04554

PCT Pub. Date: Feb. 5, 1998

[30] Foreign Application Priority Data

Jul. 29, 1996 [JP] Japan ................................. 8-216019
Dec. 2, 1996 [JP] Japan ................................. 8-336357

[51] Int. Cl.[7] ................ A61K 31/453; A61K 31/4535; A61K 31/439; C07D 405/12; C07D 409/12; C07D 451/14

[52] U.S. Cl. .................... 514/299; 514/217.11; 514/304; 514/318; 514/320; 514/324; 514/325; 514/422; 544/596; 546/112; 546/126; 546/194; 546/196; 546/202; 546/204; 548/525

[58] Field of Search .................... 546/112, 194, 546/196, 202, 204, 126; 514/299, 318, 320, 324, 325, 304

[56] References Cited

FOREIGN PATENT DOCUMENTS

| | | |
|---|---|---|
| 502788 | 9/1992 | European Pat. Off. |
| 95/01350 | 1/1995 | WIPO |
| 96/05837 | 2/1996 | WIPO |

OTHER PUBLICATIONS

Rico B et al. J. Heterocycl. Chem. 31(2), 313–18, 1994.
Hesselgesser J et al. J. Biol. Chem. 273(25), 15687–15692, Jun. 1998.
Cocchi et al. Science 270, pp. 1811–1815, 1995.
Dragic et al. Nature 381, pp. 667–673, Jun. 1996.

*Primary Examiner*—Evelyn Mei Huang
*Attorney, Agent, or Firm*—Oblon, Spivak, McClelland, Maier & Neustadt, P.C.

[57] ABSTRACT

The present invention relates to a compound of the general formula:

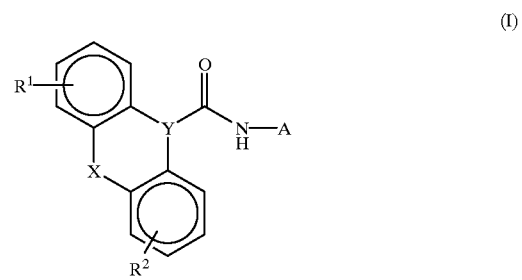

(I)

wherein each of $R^1$ and $R^2$ which may be the same or different, is e.g. a hydrogen atom, a halogen atom or a lower alkyl group, X is an oxygen atom, a sulfur atom or CH, Y is CH or a nitrogen atom, and A is e.g. a 1-substituted-4-piperidinyl group, a pharmaceutically acceptable salt thereof, a pharmaceutically acceptable anion-exchange product thereof or a hydrate thereof. The compounds of the present invention have chemokine receptor antagonism, and thus they are useful as treating agents for various diseases relating to chemokine, such as acute inflammatory diseases, chronic inflammatory diseases, acquired immune deficiency syndrome, cancer, ischemic reflow disorder and/or arteriosclerosis.

12 Claims, No Drawings

CHEMOKINE RECEPTOR ANTAGONISTS

This application is the national phase of PCT/JP97/02548, filed on Jul. 23, 1997.

TECHNICAL FIELD

The present invention relates to novel compounds having antagonism against chemokines which are leukocytic migration factors, methods for producing them, and their use.

The compounds of the present invention have high affinity to chemokine receptors. By inhibiting the action of the chemokine receptors, they can be useful in the field of pharmaceuticals, to prevent or treat e.g. acute or chronic inflammatory diseases such as septicemia, pneumonia, arthritis or allergic diseases, acquired immune deficiency syndrome, cancer, ischemic reflow disorder, arteriosclerosis, or rejection symptoms after organ transplantation operation.

BACKGROUND ART

Chemokines are polypeptidic leukocytic migration factors having molecular weights of about 10,000, and at least 21 types of peptide families having similar structures have been found. Further, at least 7 types of the chemokine receptors to which chemokines bind exist on leukocyte, and the receptors are considered to play an important role by means of selective migration and activation of leukocyte in many inflammatory diseases [Trends in Pharmacological Sciences, 17, 209–213 (1996)].

Accordingly, substances which specifically inhibit binding of chemokines to the chemokine receptors are considered to suppress the selective migration and activation of leukocyte and thus be useful as pharmaceutical drugs for prevention or treatment of e.g. acute or chronic inflammatory diseases such as septicemia, pneumonia, arthritis or allergic diseases, cancer, ischemic reflow disorder, arteriosclerosis, or rejection symptoms after organ transplantation operation.

Further, in recent years, the chemokine receptors have been identified to be receptors on target cells, which are important for AIDS virus (HIV) to infect to the target cells [Nature, 381, 661–666 (1996); Nature, 381, 667–673 (1996); Cell, 85, 1149–1158 (1996)]. Further, it was clarified that chemokines and chemokines which lack an amino acid residue on the amino terminal inhibit infection of HIV to the target cells [Science, 270, 1811–1815 (1995); Nature, 383, 400 (1996)].

Accordingly, substances which specifically inhibit functions of the chemokine receptors are considered to inhibit infection of HIV to the target cells and thus be useful as pharmaceutical drugs for prevention or treatment of acquired immune deficiency syndrome.

DISCLOSURE OF THE INVENTION

The present invention provides a compound of the general formula:

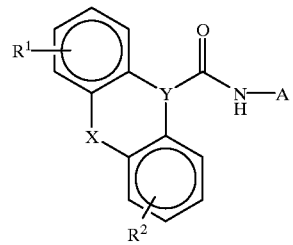

(I)

wherein each of $R^1$ and $R^2$ which may be the same or different, is a hydrogen atom, a halogen atom, a lower alkyl group, a lower alkenyl group, a lower alkynyl group, a hydroxy lower alkyl group, a lower alkoxy group, a lower alkoxycarbonyl group, an aralkyloxycarbonyl group, a formyl group, a carbamoyl group, a lower alkylaminocarbonyl group, a di-lower alkylaminocarbonyl group, a lower alkoxycarbonyl(lower)alkylaminocarbonyl group, an aralkyloxycarbonyl(lower)alkylaminocarbonyl group, an aralkylaminocarbonyl group, diaralkylaminocarbonyl group or a heteroaryl(lower)alkylaminocarbonyl group (wherein a heteroaryl group of the said heteroaryl(lower)alkylaminocarbonyl group contains one to three hetero atoms selected from the group consisting of an oxygen atom, a nitrogen atom and a sulfur atom, and when it contains at least one nitrogen atom, it may form a quaternary salt with a lower alkyl group or a lower alkenyl group), X is an oxygen atom, a sulfur atom or CH, Y is CH or a nitrogen atom, A is a group of the formula:

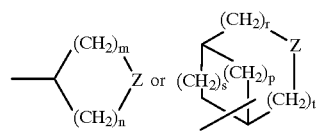

wherein each of m and n is from 1 to 3, m+n is from 3 to 5, p is from 1 to 3, each of r, s and t which may be the same or different, is from 0 to 3, r+s+t is from 2 to 3, and Z is a group of the formula:

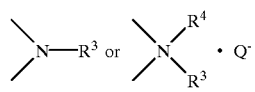

wherein $R^3$ is a $C_{5-15}$ saturated or unsaturated aliphatic hydrocarbon group, $R^4$ is a lower alkyl group or a lower alkenyl group, and $Q^-$ is an anion, a pharmaceutically acceptable salt thereof, a pharmaceutically acceptable anion-exchange product thereof or a hydrate thereof.

The compounds of the above formula [1] provided by the present invention have chemokine receptor antagonism, and thus they are highly useful for prevention or treatment of e.g. acute or chronic inflammatory diseases such as septicemia, pneumonia, arthritis or allergic diseases, acquired immune deficiency syndrome, cancer, ischemic reflow disorder, arteriosclerosis, rejection symptoms after organ transplantation operation.

Now, terms used in the present specification will be described, and the present invention will be explained in further detail. The term "a halogen atom" includes a fluorine atom, a chlorine atom, a bromine atom and an iodine atom.

The term "a lower alkyl group" means a $C_{1-6}$ linear or branched alkyl group such as a methyl group, an ethyl group, a propyl group, an isopropyl group, a butyl group, a sec-butyl group, an isobutyl group, a t-butyl group, a pentyl group, an isopentyl group, a hexyl group or an isohexyl group.

The term "a hydroxy lower alkyl group" means a $C_{1-6}$ linear or branched hydroxyalkyl group such as a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 1-hydroxypentyl group, a 2-hydroxypentyl group, a 1-hydroxyhexyl group, a 2-hydroxyhexyl group or a 1-hydroxyhexyl group.

"A lower alkoxy group" means a $C_{1-6}$ linear or branched alkoxy group such as a methoxy group, an ethoxy group, a propoxy group, an isopropoxy group, a butoxy group, a sec-butoxy group, a t-butoxy group, a pentyloxy group, an isopentyloxy group, a hexyloxy group or an isohexyloxy group.

"A lower alkoxycarbonyl group" means a $C_{2-7}$ linear or branched lower alkoxycarbonyl group such as a methoxycarbonyl group, an ethoxycarbonyl group, a propoxycarbonyl group, an isopropoxycarbonyl group, a butoxycarbonyl group, a sec-butoxycarbonyl group, a t-butoxycarbonyl group, a pentyloxycarbonyl group, an isopentyloxycarbonyl group, a hexyloxycarbonyl group or an isohexyloxycarbonyl group.

"An aralkyloxycarbonyl group" means a $C_{7-12}$ aralkyloxycarbonyl group such as a benzyloxycarbonyl group, a phenethyloxycarbonyl group, a phenylpropyloxycarbonyl group or a naphthyloxycarbonyl group.

"A lower alkylaminocarbonyl group" means an alkylaminocarbonyl group having a $C_{1-6}$ linear or branched alkyl group, such as a methylaminocarbonyl group, an ethylaminocarbonyl group, a propylaminocarbonyl group, an isopropylaminocarbonyl group, a butylaminocarbonyl group, a sec-butylaminocarbonyl group, an isobutylaminocarbonyl group, a t-butylaminocarbonyl group, a pentylaminocarbonyl group, an isopentylaminocarbonyl group, a hexylaminocarbonyl group or an isohexylaminocarbonyl group.

"A di-lower alkylaminocarbonyl group" means a dialkylaminocarbonyl group having two $C_{1-6}$ linear or branched alkyl groups on N, such as a dimethylaminocarbonyl group, an ethylmethylaminocarbonyl group, a diethylaminocarbonyl group, a dipropylaminocarbonyl group, a methylpropylaminocarbonyl group, a diisopropylaminocarbonyl group, a dibutylaminocarbonyl group, a di-sec-butylaminocarbonyl group, a diisobutylaminocarbonyl group, a methyl(t-butyl)aminocarbonyl group, a methylpentylaminocarbonyl group, an isopentylmethylaminocarbonyl group, a hexylmethylaminocarbonyl group or an isohexylmethylaminocarbonyl group.

"A lower alkoxycarbonyl(lower)alkylaminocarbonyl group" may, for example, be a (methoxycarbonylmethyl)aminocarbonyl group, an (ethoxycarbonylmethyl)aminocarbonyl group, a (propoxycarbonylmethyl)aminocarbonyl group, an (isopropoxycarbonylmethyl)aminocarbonyl group, a (butoxycarbonylmethyl)aminocarbonyl group, a (sec-butoxycarbonylmethyl)aminocarbonyl group, a (t-butoxycarbonylmethyl)aminocarbonyl group, a (pentyloxycarbonylmethyl)aminocarbonyl group, an (isopentyloxycarbonylmethyl)aminocarbonyl group, a (hexyloxycarbonylmethyl)aminocarbonyl group, an (isohexyloxycarbonylmethyl)aminocarbonyl group, a (methoxycarbonylethyl)aminocarbonyl group, an (ethoxycarbonylethyl)aminocarbonyl group, an (ethoxycarbonylpropyl)aminocarbonyl group or an (ethoxycarbonylbutyl)aminocarbonyl group.

"A lower aralkyloxycarbonyl(lower)alkylaminocarbonyl group" may, for example, be a (benzyloxycarbonylmethyl)aminocarbonyl group, a (phenethyloxycarbonylmethyl)aminocarbonyl group or a (phenylpropyloxycarbonylmethyl)aminocarbonyl group.

"An aralkylaminocarbonyl group" may, for example, be a benzylaminocarbonyl group, a phenethylaminocarbonyl group or a phenylpropylaminocarbonyl group.

"A diaralkylaminocarbonyl group" may, for example, be a dibenzylaminocarbonyl group, a benzylphenethylaminocarbonyl group or a benzylphenylpropylaminocarbonyl group.

"A heteroaryl(lower)alkylaminocarbonyl group" means a heteroaryl(lower)alkylaminocarbonyl group having heteroaryl containing one to three hetero atoms selected from the group consisting of an oxygen atom, a nitrogen atom and a sulfur atom, such as a 2-pyridylmethylaminocarbonyl group, a 3-pyridylmethylaminocarbonyl group, a 4-pyridylmethylaminocarbonyl group, a 2-thiazolylmethylaminocarbonyl group, a 2-thienylmethylaminocarbonyl group, a 3-thienylmethylaminocarbonyl group, a 1-imidazolylmethylaminocarbonyl group, a 2-imidazolylmethylaminocarbonyl group, a 4-imidazolylmethylaminocarbonyl group, a 3-pyrazolylmethylaminocarbonyl group, a 4-pyrazolylmethylaminocarbonyl group, a 2-furylmethylaminocarbonyl group, a 3-furylmethylaminocarbonyl group, a 2-pyrrolylmethylaminocarbonyl group, a 3-pyrrolylmethylaminocarbonyl group, a 2-pyrimidinylmethylaminocarbonyl group, a 4-pyrimidinylmethylaminocarbonyl group, a 5-pyrimidinylmethylaminocarbonyl group, a 2-pyrazinylmethylaminocarbonyl group, a 3-pyridazinylmethylaminocarbonyl group, a 4-pyridazinylmethylaminocarbonyl group, a 2-quinolinylmethylaminocarbonyl group, a 2-benzothienylmethylaminocarbonyl group, a 2-indolylmethylaminocarbonyl group, a 2-pyridylethylaminocarbonyl group, a 3-pyridylethylaminocarbonyl group, a 4-pyridylethylaminocarbonyl group, a 2-thiazolylethylaminocarbonyl group, a 2-thienylethylaminocarbonyl group, a 3-thienylethylaminocarbonyl group, a 1-imidazolylethylaminocarbonyl group, a 2-imidazolylethylaminocarbonyl group, a 4-imidazolylethylaminocarbonyl group, a 3-pyrazolylethylaminocarbonyl group, a 4-pyrazolylethylaminocarbonyl group, a 2-furylethylaminocarbonyl group, a 3-furylethylaminocarbonyl group, a 2-pyrrolylethylaminocarbonyl group, a 3-pyrrolylethylaminocarbonyl group, a 2-pyrimidinylethylaminocarbonyl group, a 4-pyrimidinylethylaminocarbonyl group, a 5-pyrimidinylethylaminocarbonyl group, a 2-pyrazinylethylaminocarbonyl group, a 3-pyridazinylethylaminocarbonyl group, a 4-pyridazinylethylaminocarbonyl group, a 2-quinolinylethylaminocarbonyl group, a 2-benzothienylethylaminocarbonyl group, a 2-indolylethylaminocarbonyl group, a 2-pyridylpropylaminocarbonyl group, a 2-pyridylbutylaminocarbonyl group or a 2-pyridylpentylaminocarbonyl group.

The term "a lower alkenyl group" means a $C_{2-6}$ linear or branched alkenyl group such as an ethenyl group, a propenyl group, an isopropenyl group, a 1-methyl-1-propenyl group, a 1-ethyl-1-propenyl group, a 1-methyl-2-propenyl group, a 1-butenyl group, a 2-butenyl group, a 3-butenyl group, a 1-methyl-2-butenyl group, a 1-methyl-3-butenyl group, a 1-pentenyl group, a 2-pentenyl group, a 3-pentenyl group, a 4-pentenyl group, a 1-hexenyl group, a 2-hexenyl group, a 3-hexenyl group, a 4-hexenyl group or a 5-hexenyl group.

The term "a lower alkynyl group" means a $C_{2-6}$ linear or branched alkenyl group such as an ethynyl group, a 1-propynyl group, a 2-propynyl group, a 1-butynyl group, a 2-butynyl group, a 3-butynyl group, a 3-methyl-1-butynyl group, a 1-pentynyl group or a 1-hexynyl group.

"A lower alkoxy group" means a $C_{1-6}$ linear or branched alkoxy group such as a methoxy group, an ethoxy group, a propoxy group, an isopropoxy group, a butoxy group, a sec-butoxy group, a t-butoxy group, a pentyloxy group, an isopentyloxy group, a hexyloxy group or an isohexyloxy group.

"A $C_{5-15}$ saturated or unsaturated aliphatic hydrocarbon group" includes a $C_{5-15}$ alkyl group, alkenyl group and alkynyl group, a cycloalkylalkyl group and a cycloalkylalkenyl group, which may have a hydrogen atom in the cycloalkyl ring substituted by lower alkyl, a bicycloalkylalkyl group and a bicycloalkylalkenyl group, which may have a hydrogen atom in the bicycloalkyl ring substituted by lower alkyl, a cycloalkenylalkyl group and a cycloalkenylalkenyl group, which may have a hydrogen atom in the cycloalkenyl ring substituted by lower alkyl, a bicycloalkenylalkyl group and a bicycloalkenylalkenyl group, which may have a hydrogen atom substituted by lower alkyl in the bicycloalkenyl ring, a cycloalkylalkynyl group and a cycloalkenylalkynyl group.

Specific examples of such an aliphatic hydrocarbon group include an alkyl group such as a 1-methylbutyl group, a 2-methylbutyl group, a 3-methylbutyl group, a pentyl group, a neopentyl group, a tert-pentyl group, a 1-methylpentyl group, a 2-methylpentyl group, a 3-methylpentyl group, a 4-methylpentyl group, a hexyl group, a 1-methylhexyl group, a 2-methylhexyl group, a 3-methylhexyl group, a 4-methylhexyl group, a 5-methylhexyl group, a 2,4-dimethylpentyl group, a 2-ethylhexyl group, a 4,5-dimethylhexyl group, a 4,4-dimethylpentyl group, a heptyl group, a 4-methylheptyl group, an octyl group, a nonyl group, a decyl group, an undecyl group, a dodecyl group, a tridecyl group, a tetradecyl group or a pentadecyl group;

an alkenyl group such as a 3-methyl-2-butenyl group, a 2-pentenyl group, a 3-pentenyl group, a 4-pentenyl group, a 3-methyl-2-pentenyl group, a 3-methyl-3-pentenyl group, a 4-methyl-2-pentenyl group, a 4-methyl-3-pentenyl group, a 4-methyl-4-pentenyl group, a 2-hexenyl group, a 3-hexenyl group, a 4-hexenyl group, a 4-methyl-2-hexenyl group, a 4-methyl-3-hexenyl group, a 4-methyl-4-hexenyl group, a 5-methyl-2-hexenyl group, a 5-methyl-3-hexenyl group, a 5-methyl-4-hexenyl group, a 5-methyl-2-heptenyl group, a 5-methyl-3-heptenyl group, a 5-methyl-4-heptenyl group, a 5-methyl-5-heptenyl group, a 3,4-dimethyl-2-pentenyl group, a 3,5-dimethyl-2-hexenyl group, a 4,5-dimethyl-2-hexenyl group, a 4,5-dimethyl-3-hexenyl group, a 4,5-dimethyl-4-hexenyl group, an octenyl group, a nonenyl group, a decenyl group, an undecenyl group, a dodecenyl group, a tridecenyl group, a tetradecenyl group or a pentadecenyl group;

an alkynyl group such as a 2-pentynyl group, a 3-pentynyl group, a 4-pentynyl group, a 4-methyl-2-pentynyl group, an octynyl group, a nonynyl group, a decynyl group, an undecynyl group, a dodecynyl group, a tridecynyl group, a tetradecynyl group or a pentadecynyl group;

a cycloalkylalkyl group which may have a hydrogen atom in the cycloalkyl ring substituted by lower alkyl, such as a cyclopropylethyl group, a cyclopropylpropyl group, a cyclpropylbutyl group, a cyclopropylpentyl group, a cyclopropylhexyl group, a cyclopropylheptyl group, a cyclobutylmethyl group, a cyclobutylethyl group, a cyclobutylpropyl group, a cyclobutylbutyl group, a cyclobutylpentyl group, a cyclopentylmethyl group, a cyclopentylethyl group, a cyclopentylpropyl group, a cyclopentylbutyl group, a cyclohexylmethyl group, a cyclohexylethyl group, a cyclohexylpropyl group, a cyclohexylbutyl group, a cycloheptylmethyl group, a cycloheptylethyl group, a cycloheptylpropyl group, a cycloheptylbutyl group, a cyclooctylmethyl group, a cyclooctylethyl group, a cyclooctylpropyl group, a cyclooctylbutyl group, a cyclononylmethyl group, a cyclononylethyl group, a cyclononylpropyl group, a cyclononylbutyl group, a cyclodecylmethyl group, a cyclodecylethyl group, a cyclodecylpropyl group, a cyclodecylbutyl group, a cycloundecylmethyl group, a cycloundecylethyl group, a cycloundecylpropyl group, a cyclodecylbutyl group, a 1-methylcyclopentylmethyl group, a 2-methylcyclopentylmethyl group, a 3-methylcyclopentylethyl group, a 1-ethylcyclopentylmethyl group, a 2-ethylcyclopentylmethyl group, a 3-ethylcyclopentylmethyl group, a 2-cyclopentylethyl group, a 2-(1-methylcyclopentyl)ethyl group, a 2-(2-methylcyclopentyl)ethyl group, a 2-(3-methylcyclopentyl)ethyl group, a 2-(1-ethylcyclopentyl)ethyl group, a 2-(2-ethylcyclopentyl)ethyl group, a 2-(3-ethylcyclopentyl)ethyl group, a 1-methylcyclohexylmethyl group, a 2-methylcyclohexylmethyl group, a 3-methylcyclohexylmethyl group, a 4-methylcyclohexylmethyl group, a 1-ethylcyclohexylmethyl group, a 2-ethylcyclohexylmethyl group, a 3-ethylcyclohexylmethyl group, a 4-ethylcyclohexylmethyl group, a cyclohexylethyl group, a 2-(1-methylcyclohexyl)ethyl group, a 2-(2-methylcyclohexyl)ethyl group, a 2-(3-methylcyclohexyl)ethyl group, a 2-(4-methylcyclohexyl)ethyl group, a 2-(1-ethylcyclohexyl) ethyl group, a 2-(2-ethylcyclohexyl)ethyl group, a 2-(3-ethylcyclohexyl)ethyl group, a 2-(4-ethylcyclohexyl) ethyl group, a 1-methylcycloheptylmethyl group, a 2-methylcycloheptylmethyl group, a 3-methylcycloheptylmethyl group, a 4-methylcycloheptylmethyl group, a 1-ethylcycloheptylmethyl group, a 2-ethylcycloheptylmethyl group, a 3-ethylcycloheptylmethyl group, a 4-ethylcycloheptylmethyl group, a 2-cycloheptylethyl group, a 2-(1-methylcycloheptyl)ethyl group, a 2-(1-methylcycloheptyl)ethyl group, a 2-(2- methylcycloheptyl)ethyl group, a 2-(3-methylcycloheptyl)ethyl group, a 2-(4-methylcycloheptyl)ethyl group, a 2-(1-ethylcycloheptyl)ethyl group, a 2-(2-ethylcycloheptyl)ethyl group, a 2-(3-ethylcycloheptyl)ethyl group, a 2-(4-ethylcycloheptyl)ethyl group, a 1-methylcyclooctylmethyl group, a 2-methylcyclooctylmethyl group, a 3-methylcyclooctylmethyl group, a 4-methylcyclooctylmethyl group, a 5-methylcyclooctylmethyl group, a 1-ethylcyclooctylmethyl group, a 2-ethylcyclooctylmethyl group, a 3-ethylcyclooctylmethyl group, a 4-ethylcyclooctylmethyl group, a 5-ethylcyclooctylmethyl group, a 2-(1-methylcyclooctyl)ethyl group, a 2-(2-methylcyclooctyl)ethyl group, a 2-(3-methylcyclooctyl)ethyl group, a 2-(4-methylcyclooctyl)ethyl group, a 2-(5-methylcyclooctyl)ethyl group, a 2-(1-ethylcyclooctyl)ethyl group, a 2-(2-ethylcyclooctyl)ethyl group, a 2-(3-ethylcyclooctyl)ethyl group, a 2-(4-ethylcyclooctyl)ethyl group or a 2-(5-ethylcyclooctyl)ethyl group;

a cycloalkylalkenyl group such as cyclopropylpropenyl, a cyclopropylbutenyl group, a cyclopropylpentenyl group, a cyclopropylhexenyl group, a cyclopropylheptenyl group, a cyclobutylpropenyl group, a cyclobutylbutenyl group, a cyclobutylpentenyl group, a cyclopentylpropenyl group, a cyclopentylbutenyl group, a cyclopentylpentenyl group, a cyclohexylpropenyl group, a cyclohexylbutenyl group, a cyclohexylpentenyl group, a cycloheptylpropenyl group or a cyclooctylpropenyl group;

a bicycloalkylalkyl group which may have a hydrogen atom in the bicycloalkyl ring substituted by lower alkyl, such as a bicyclo[4.1.0]hept-1-ylmethyl group, a bicyclo[4.1.0]hept-2-ylmethyl group, a bicyclo[4.1.0]hept-3-ylmethyl group, a bicyclo[4.1.0]hept-7-ylmethyl group, a bicyclo[3.3.0]oct-1-ylmethyl group, a bicyclo[3.3.0]oct-2-ylmethyl group, a bicyclo[3.3.0]oct-3-ylmethyl group, a bicyclo[4.1.0]hept-1-ylethyl group, a bicyclo[4.1.0]hept-2-ylethyl group, a bicyclo[4.1.0]hept-3-ylethyl group, a bicyclo[4.1.0]hept-7-ylethyl group, a bicyclo[3.3.0]oct-1-ylethyl group, a bicyclo[3.3.0]oct-2-ylethyl group, a bicyclo[3.3.0]oct-3-ylethyl group, a bicyclo[3.2.1]oct-1-ylmethyl group, a bicyclo[3.2.1]oct-2-ylmethyl group, a bicyclo[3.2.1]oct-3-ylmethyl group, a bicyclo[3.2.1]oct-8-ylmethyl group, a bicyclo[4.4.0]dec-1-ylmethyl group, a bicyclo[4.4.0]dec-2-ylmethyl group, a bicyclo[4.4.0]dec-3-ylmethyl group, a bicyclo[4.3.0]non-1-ylmethyl group, a bicyclo[4.3.0]non-2-ylmethyl group, a bicyclo[4.3.0]non-3-ylmethyl group, a bicyclo[4.3.0]non-7-ylmethyl group, a bicyclo[3.3.1]non-1-ylmethyl group, a bicyclo[3.3.1]non-2-ylmethyl group, a bicyclo[3.3.1]non-3-ylmethyl group, a bicyclo[3.3.1]non-9-ylmethyl group, a bicyclo[3.1.0]hex-1-ylmethyl group, a bicyclo[3.1.0]hex-2-ylmethyl group, a bicyclo[3.1.0]hex-3-ylmethyl group or a bicyclo[3.1.0]hex-6-ylmethyl group;

a bicycloalkylalkenyl group which may have a hydrogen atom in the bicycloalkyl ring substituted by lower alkyl, such as a bicyclo[4.1.0]hept-1-ylethenyl group, a bicyclo[4.1.0]hept-2-ylethenyl group, a bicyclo[4.1.0]hept-3-ylethenyl group or a bicyclo[4.1.0]hept-7-ylethenyl group;

a cycloalkylalkynyl group such as cyclopropylpropynyl, a cyclopropylbutynyl group, a cyclopropylpentynyl group, a cyclopropylhexynyl group, a cyclopropylheptynyl group, a cyclobutylpropynyl group, a cyclobutylbutynyl group, a cyclobutylpentynyl group, a cyclopentylpropynyl group, a cyclopentylbutynyl group, a cyclopentylpentynyl group, a cyclohexylpropynyl group, a cyclohexylbutynyl group or a cyclohexylpentynyl group;

a cycloalkenylalkyl group which may have a hydrogen atom in the cycloalkenyl ring substituted by lower alkyl, such as a (1-cyclopropenyl)ethyl group, a (2-cyclopropenyl)ethyl group, a (1-cyclopropenyl)propyl group, a (2-cyclopropenyl)propyl group, a (1-cyclopropenyl)butyl group, a (2-cyclopropenyl)butyl group, a (1-cyclopropenyl)pentyl group, a (2-cyclopropenyl)pentyl group, a (1-cyclopropenyl)hexyl group, a (2-cyclopropenyl)hexyl group, a (1-cyclopropenyl)heptyl group, a (2-cyclopropenyl)heptyl group, a (1-cyclobutenyl)methyl group, a (2-cyclobutenyl)methyl group, a (1-cyclobutenyl)ethyl group, a (2-cyclobutenyl)ethyl group, a (1-cyclobutenyl)propyl group, a (2-cyclobutenyl)propyl group, a (1-cyclopentenyl)methyl group, a (2-cyclopentenyl)methyl group, a (3-cyclopentenyl)methyl group, a (1-cyclohexenyl)methyl group, a (2-cyclohexenyl)methyl group, a (3-cyclohexenyl)methyl group, a (1-cyclohexenyl)ethyl group, a (2-cyclohexenyl)ethyl group, a (3-cyclohexenyl)ethyl group, a (1-cycloheptenyl)methyl group, a (2-cycloheptenyl)methyl group, a (4-cycloheptenyl)methyl group, a (1-cycloheptenyl)ethyl group, a (2-cycloheptenyl)ethyl group, a (3-cycloheptenyl)ethyl group, a (4-cycloheptenyl)ethyl group, a (1-cyclooctenyl)methyl group, a (2-cyclooctenyl)methyl group, a (3-cyclooctenyl)methyl group, a (4-cyclooctenyl)methyl group, a (1-cyclooctenyl)ethyl group, a (2-cyclooctenyl)ethyl group, a (4-cyclooctenyl)ethyl group, a (4-cyclooctenyl)ethyl group, a (1-cyclononenyl)methyl group, a (2-cyclononenyl)methyl group, a (3-cyclononenyl)methyl group, a (4-cyclononenyl)methyl group, a (5-cyclononenyl)methyl group, a (1-cyclononenyl)ethyl group, a (2-cyclononenyl)ethyl group, a (3-cyclononenyl)ethyl group, a (4-cyclononenyl) ethyl group, a (5-cyclononenyl)ethyl group, a (1-cyclodecenyl)methyl group, a (2-cyclodecenyl)methyl group, a (3-cyclodecenyl)methyl group, a (4-cyclodecenyl)methyl group, a (5-cyclodecenyl)methyl group, a (1-cyclodecenyl)ethyl group, a (2-cyclodecenyl)ethyl group, a (3-cyclodecenyl)methyl group, a (4-cyclodecenyl)ethyl group, a (5-cyclodecenyl)ethyl group, a (1-cycloundecenyl)methyl group, a (2-cycloundecenyl)methyl group, a (3-cycloundecenyl)methyl group, a (4-cycloundecenyl)methyl group, a (5-cycloundecenyl)methyl group, a (6-cycloundecenyl)methyl group, a (1-cycloundecenyl)ethyl group, a (2-cycloundecenyl)ethyl group, a (3-cycloundecenyl)ethyl group, a (4-cycloundecenyl)ethyl group, a (5-cycloundecenyl)ethyl group, a (6-cycloundecenyl)ethyl group, a (1-methyl-2-cyclopentenyl)methyl group, a (1-methyl-3-cyclopentenyl)methyl group, a (2-methyl-1-cyclopentenyl)methyl group, a (2-methyl-2-cyclopentenyl)methyl group, a (2-methyl-3-cyclopentenyl)methyl group, a (5-methyl-2-cyclopentenyl)methyl group, a (5-methyl-1-cyclopentenyl)methyl group, a (3-methyl-1-cyclopentenyl)methyl group, a (3-methyl-2- cyclopentenyl)methyl group, a (3-methyl-3-cyclopentenyl)methyl group, a (4-methyl-2-cyclopentenyl)methyl group, a (4-methyl-1-cyclopentenyl)methyl group, a (1-methyl-2-cyclohexenyl)methyl group, a (1-methyl-3-cyclohexenyl)methyl group, a (2-methyl-1-cyclohexenyl)methyl group, a (2-methyl-2-cyclohexenyl)methyl group, a (2-methyl-3-cyclohexenyl)methyl group, a (6-methyl-3-cyclohexenyl)methyl group, a (6-methyl-2-cyclohexenyl)methyl group, a (6-methyl-1-cyclohexenyl)methyl group, a (3-methyl-1-cyclohexenyl)methyl group, a (3-methyl-2-cyclohexenyl)methyl group, a (3-methyl-3-cyclohexenyl)methyl group, a (5-methyl-3-cyclohexenyl)methyl group, a (5-methyl-2-cyclohexenyl)methyl group, a (5-methyl-1-cyclohexenyl)methyl group, a (4-methyl-1-cyclohexenyl)methyl group, a (4-methyl-2-cyclohexenyl)methyl group, a (4-methyl-3-cyclohexenyl)methyl group, a (1-methyl-2-cycloheptenyl)methyl group, a (1-methyl-3-cycloheptenyl)methyl group, a (1-methyl-4-cycloheptenyl)methyl group, a (2-methyl-1-cycloheptenyl)methyl group, a (2-methyl-2-cycloheptenyl)methyl group, a (2-methyl-3-cycloheptenyl)methyl group, a (2-methyl-4-cycloheptenyl)methyl group, a (7-methyl-3-cycloheptenyl)methyl group, a (7-methyl-2-cycloheptenyl)methyl group, a (7-methyl-1-cycloheptenyl)methyl group, a (3-methyl-1-cycloheptenyl)methyl group, a (3-methyl-2-cycloheptenyl)methyl group, a (3-methyl-3-cycloheptenyl)methyl group, a (3-methyl-4-cycloheptenyl)methyl group, a (6-methyl-3-cycloheptenyl)methyl group, a (6-methyl-2-cycloheptenyl)methyl group, a (6-methyl-1-cycloheptenyl)methyl group, a (4-methyl-1-cycloheptenyl)methyl group, a (4-methyl-2-cycloheptenyl)methyl group, a (4-methyl-3-cycloheptenyl)methyl group, a (4-methyl-4-cycloheptenyl)methyl group, a (5-methyl-3-cycloheptenyl)methyl group, a (5-methyl-2-cycloheptenyl)methyl group, a (5-methyl-1-cycloheptenyl)methyl group, a (1-methyl-2-cyclooctenyl)methyl group, a (1-methyl-3-cyclooctenyl)methyl group, a (1-methyl-4-cyclooctenyl)methyl group, a (2-methyl-1-cyclooctenyl)methyl group, a (2-methyl-2-cyclooctenyl)methyl group, a (2-methyl-3-cyclooctenyl)methyl group, a (2-methyl-4-cyclooctenyl)methyl group, a (8-methyl-4-cyclooctenyl)methyl group, a (8-methyl-3-cyclooctenyl)methyl group, a (8-methyl-2-cyclooctenyl)methyl group, a (8-methyl-1-cyclooctenyl)methyl group, a (3-methyl-1-cyclooctenyl)methyl group, a (3-methyl-2-cyclooctenyl)methyl group, a (3-methyl-3-cyclooctenyl)methyl group, a (3-methyl-4-cyclooctenyl)methyl group, a (7-methyl-4-cyclooctenyl)methyl group, a (7-methyl-3-cyclooctenyl)methyl group, a (7-methyl-2-cyclooctenyl)methyl group, a (7-methyl-1-cyclooctenyl)methyl group, a (4-methyl-1-cyclooctenyl)methyl group, a (4-methyl-2-cyclooctenyl)methyl group, a (4-methyl-3-cyclooctenyl)methyl group, a (4-methyl-4-cyclooctenyl)methyl group, a (6-methyl-4-cyclooctenyl)methyl group, a (6-methyl-2-cyclooctenyl)methyl group, a (6-methyl-2-cyclooctenyl)methyl group, a (6-methyl-1-cyclooctenyl)methyl group, a (5-methyl-1-cyclooctenyl)methyl group, a (5-methyl-2-cyclooctenyl)methyl group, a (5-methyl-3-cyclooctenyl)methyl group or a (5-methyl-4-cyclooctenyl)methyl group;

a bicycloalkenylalkyl group which may have a hydrogen atom in the bicycloalkenyl ring substituted by lower alkyl, such as a bicyclo[4.1.0]hept-2-en-1-ylmethyl group, a bicyclo[4.1.0]hept-3-en-1-ylmethyl group, a bicyclo[4.1.0]hept-4-en-1-ylmethyl group, a bicyclo[4.1.0]hept-3-en-2-ylmethyl group, a bicyclo[4.1.0]hept-4-en-2-ylmethyl group, a bicyclo[4.1.0]hept-2-en-3-ylmethyl group, a bicyclo[4.1.0]hept-3-en-3-ylmethyl group, a bicyclo[4.1.0]hept-4-en-3-ylmethyl group, a bicyclo[4.1.0]hept-2-en-7-ylmethyl group, a bicyclo[3.3.0]oct-2-en-2-ylmethyl group, a bicyclo[3.3.0]oct-2-en-3-ylmethyl group, a bicyclo[4.1.0]hept-2-en-1-ylethyl group, a bicyclo[4.1.0]hept-2-en-1-ylethyl group, a bicyclo[4.1.0]hept-2-en-2-ylethyl group, a bicyclo[4.1.0]hept-2-en-3-ylethyl group, a bicyclo[4.1.0]hept-2-en-4-ylethyl group, a bicyclo[4.1.0]hept-2-en-7-ylethyl group, a bicyclo[3.3.0]oct-2-en-1-ylethyl group, a bicyclo[3.3.0]oct-2-en-2-ylethyl group or a bicyclo[3.3.0]oct-2-en-3-ylethyl group;

a bicycloalkenylalkenyl group which may have a hydrogen atom in the bicycloalkenyl ring substituted by lower alkyl, such as a bicyclo[4.1.0]hept-2-en-1-ylethenyl group, a bicyclo[4.1.0]hept-3-en-1-ylethenyl group, a bicyclo[4.1.0]hept-4-en-1-ylethenyl group, a bicyclo[4.1.0]hept-3-en-2-ylethenyl group, a bicyclo[4.1.0]hept-4-en-2-ylethenyl group, a bicyclo[4.1.0]hept-2-en-3-ylethenyl group, a bicyclo[4.1.0]hept-3-en-3-ylethenyl group, a bicyclo[4.1.0]hept-4-en-3-ylethenyl group, a bicyclo[4.1.0]hept-2-en-7-ylethenyl group, a bicyclo[3.3.0]oct-2-en-2-ylethenyl group or a bicyclo[3.3.0]oct-2-en-3-ylethenyl group;

a cycloalkenylalkenyl group such as a cyclopropenylpropenyl group, a cyclopropenylbutenyl group, a cyclobutenylbutenyl group, a cyclopentenylpropenyl group, a cyclopentenylbutenyl group, a cyclopropenylpentenyl group, a cyclopropenylhexenyl group, a cyclopropenylheptenyl group, a cyclobutenylpropenyl group, a cyclohexenylpropenyl group or a cyclohexenylbutenyl group;

and a cycloalkenylalkynyl group such as a cyclopropenylpropynyl group, a cyclopropenylbutynyl group, a cyclopropenylpentynyl group, a cyclopropenylhexynyl group, a cyclopropenylheptynyl group, a cyclobutenylpropynyl group, a cyclobutenylbutynyl group, a cyclopentenylpropynyl group, a cyclopentenylbutynyl group, a cyclohexenylpropynyl group or a cyclohexenylbutynyl group.

A group of the formula

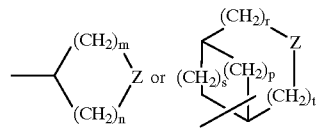

wherein m, n, p, r, s, t and Z are the same as defined above, means a monocyclic heterocyclic group having a nitrogen atom or a bicyclic heterocyclic group having a skeleton represented by the formulae:

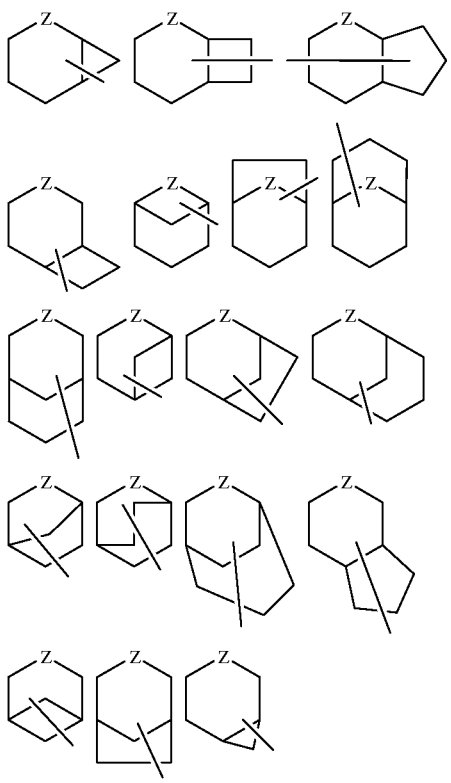

wherein Z is the same as defined above. More specifically, it may, for example, be a pyrrolidinyl group, a piperidinyl group, a hexahydroazepinyl group, a 1-azabicyclo[2.2.1]heptyl group or a 1-azabicyclo[3.2.1]octyl group or its quaternary amine salt.

"An anion" includes a halogen atom ion such as a chloride ion, a bromide ion and an iodide ion, an organic sulfonate ion such as tosylate and mesylate, an inorganic anion such as a nitrate ion, a sulfate ion, a phosphate ion and a carbonate ion, a carboxylate such as an acetate, a triflate, a propionate, an oxalate and a malonate, and an anion of an amino acid such as glutamic acid. "A phosgene" means not only a so-called phosgene but also a diphosgene and a triphosgene.

Now, the meaning of the symbols used in the general formula [I] and its specific and preferred examples will be described, and further, the present invention will be explained hereinafter.

Each of $R^1$ and $R^2$ which may be the same or different, is a hydrogen atom, a halogen atom, a lower alkyl group, a lower alkenyl group, a lower alkynyl group, a hydroxy lower alkyl group, a lower alkoxy group, a lower alkoxycarbonyl group, an aralkyloxycarbonyl group, a formyl group, a carbamoyl group, a lower alkylaminocarbonyl group, a di-lower alkylaminocarbonyl group, a lower alkoxycarbonyl (lower)alkylaminocarbonyl group, an aralkyloxycarbonyl (lower)alkylaminocarbonyl group, an aralkylaminocarbonyl group, a diaralkylaminocarbonyl group or a heteroaryl (lower)alkylaminocarbonyl group (wherein a heteroaryl group of the said heteroaryl(lower)alkylaminocarbonyl group contains 1 to 3 hetero atoms selected from the group consisting of an oxygen atom, a nitrogen atom and a sulfur atom, and when it contains at least one nitrogen atom, it may form a quaternary salt with a lower alkyl group or a lower alkenyl group). Definition and specific examples of each substituent are the same as defined above.

X means an oxygen atom, a sulfur atom or CH. Among these, an oxygen atom and a sulfur atom are preferred.

Y is CH or a nitrogen atom. Among these, CH is preferred.

A is a group represented by the formula:

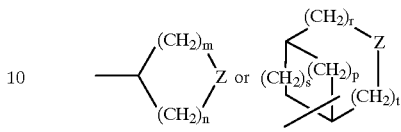

wherein each of m and n is from 1 to 3, m+n is from 3 to 5, p is from 1 to 3, each of r, s and t which may be the same or different, is from 0 to 3, r+s+t is from 2 to 3, and Z is a group represented by the formula:

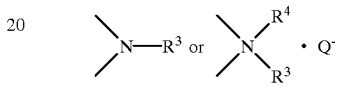

wherein $R^3$ is a $C_{5-15}$ saturated or unsaturated aliphatic hydrocarbon group, $R^4$ is a lower alkyl group or a lower alkenyl group, and $Q^-$ is an anion. The definition and specific examples of each substituent are described above.

As described above, each of m and n is from 1 to 3. Among these, preferred is a case where both m and n is 2. $R^3$ is a $C_{5-15}$ saturated or unsaturated aliphatic hydrocarbon group. Among these, a cyclooctylmethyl group, a cyclononylmethyl group, a 1-decalylmethyl group, a 2-decalylmethyl group, a (1-cyclooctenyl)methyl group and a (1-cyclononenyl)methyl group are preferred. $R^4$ is a lower alkyl group or a lower alkenyl group. Among these, a methyl group, an ethyl group, a propyl group and an allyl group are preferred.

Stereoisomers of the compounds of the present invention, such as an optical isomer, a diastereoisomer or a geometrical isomer may exist depending upon the mode of the substitution. The compounds of the present invention include such stereoisomers and their mixture.

The compounds of the present invention may exist in a form of a pharmaceutically acceptable salt. Examples of such a salt include an inorganic acid salt such as a hydrochloride, a sulfate, a nitrate, a phosphate or a perchlorate; an organic carboxylate such as a maleate, a fumarate, a succinate, a tartrate, a citrate or an ascrobate; an organic sulfonate such as a methanesulfonate, an isethionate, a benzenesulfonate or a p-toluenesulfonate.

The compounds of the present invention can be produced by the following synthetic route.

Route 1

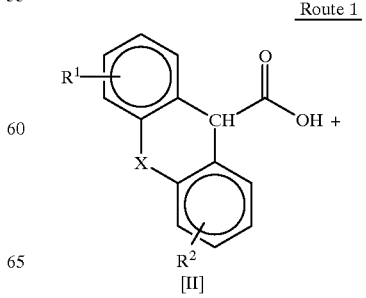

[II]

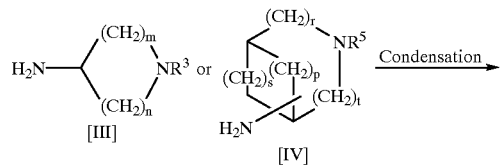
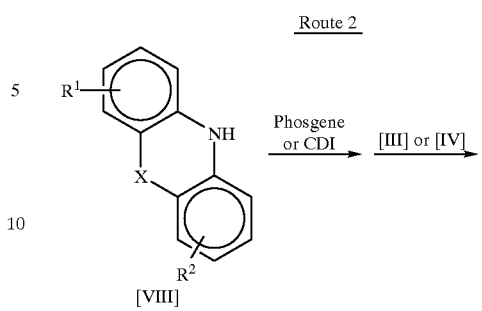
Route 2
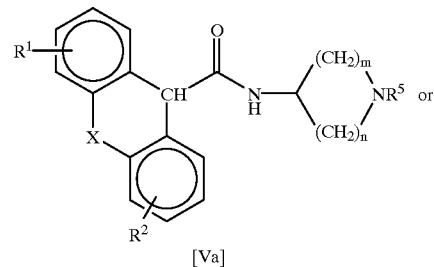
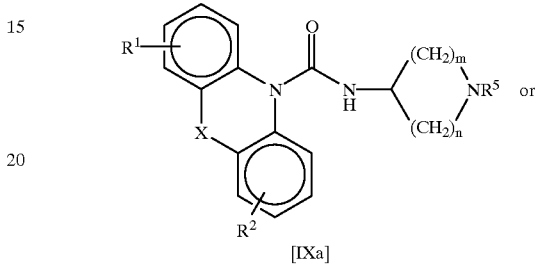
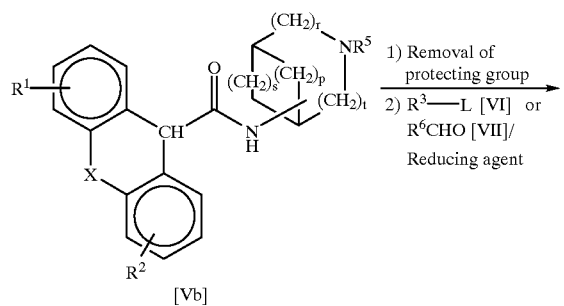
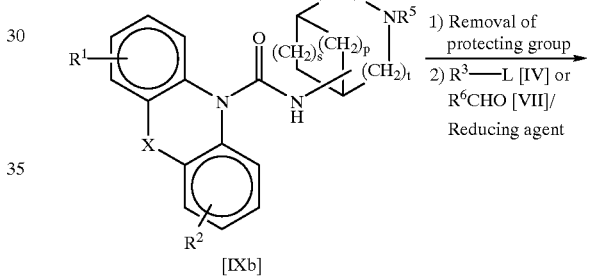
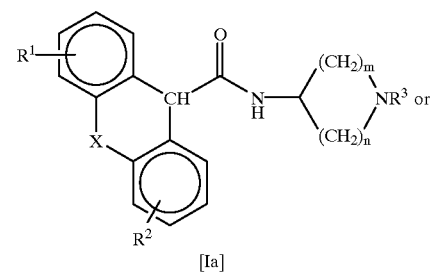
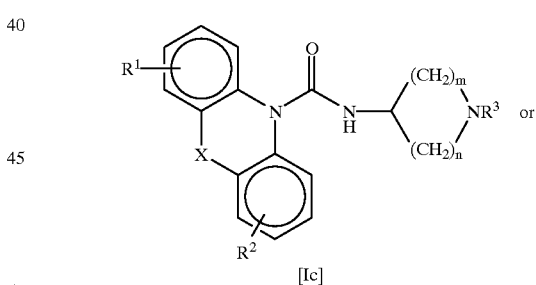
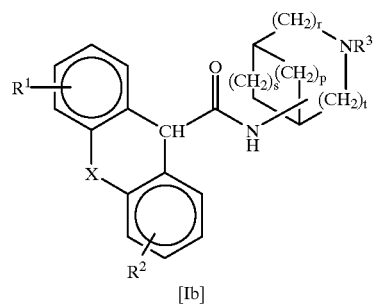
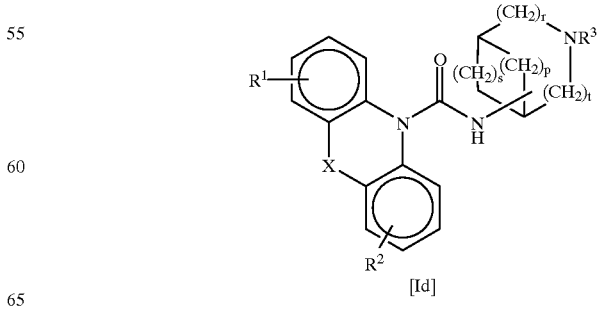

Route 3

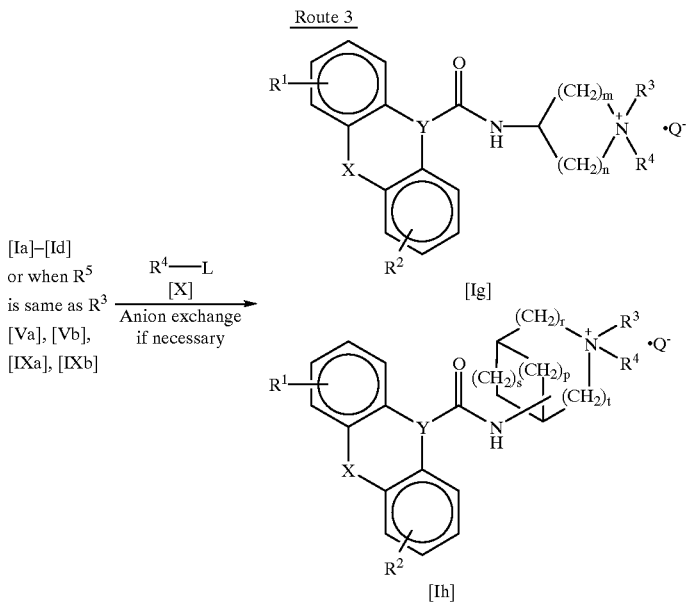

[Ia]–[Id] or when R⁵ is same as R³ [Va], [Vb], [IXa], [IXb]

wherein $R^1$, $R^2$, $R^3$, $R^4$, X, Y, $Q^-$, m, n, p, r, s and t are the same as defined above, $R^5$ is the same as $R^3$ or a protecting group, $R^6$ is a $C_{4-14}$ saturated or unsaturated aliphatic hydrocarbon group, L is a leaving group, and CDI is carbonyldiimidazole.

Now, the Routes 1 to 3 are explained in further detail.

Route 1

The reaction of the compound [II] with the compound [III] or [IV] is a condensation reaction of a carboxylic acid compound with an amino compound, which is widely known in the field of organic chemistry. It can be carried out by using a condensing agent in a suitable solvent. The condensing agent to be used may, for example, be N,N'-dicyclohexylcarbodiimide, 1-ethyl-3-(3-dimethylaminopropyl)carbodiimide, diphenylphosphorylazide or dipyridyldisulfide-triphenylphosphine. Particularly, 1-ethyl-3-(3-dimethylaminopropyl)carbodiimide is preferred.

The amount of such a condensing agent is not strictly limited. However, it is usually from 1 to 5 equivalent, particularly from 1 to 2 equivalent per mol of the compound [III] or [IV].

Further, the condensation reaction can be carried out in the presence of a base, as the case requires. The base to be used may, for example, be an aromatic amine such as pyridine, 4-dimethylaminopyridine, picoline, lutidine, quinoline or isoquinoline. Particularly, 4-dimethylaminopyridine is preferred.

The solvent may, for example, be diethyl ether, tetrahydrofuran, N,N-dimethylformamide, dioxane, benzene, toluene, chlorobenzene, methylene chloride, chloroform, carbon tetrachloride, dichloroethane or trichloroethylene, or a mixture of the solvents. Particularly, diethyl ether, tetrahydrofuran, N,N-dimethylformamide and dioxane are preferred.

The reaction temperature is usually from −70° C. to the boiling point of the solvent to be used, preferably within a range of from −20° C. to 100° C. The reaction will be finished usually in from 5 minutes to 7 days, preferably from 10 minutes to 24 hours under such a condition.

The amount of the compound [III] or [IV] to the compound [II] is not strictly limited, and it can be varied depending upon the type of the compound, the reaction condition and the like. However, the amount of the compound [III] or [IV] is usually from 1 to 5 mol, preferably from 1 to 2 mol, per mol of the compound [II].

Further, the coupling compound of the formula [Va] or [Vb] can also be obtained by converting the carboxylic acid of the formula [II] to a reactive derivative, and condensing it with the compound of the formula [III] or [IV].

The reactive derivative of carboxylic acid of the formula [II] may, for example, be a mixed acid anhydride, an active ester or an active amide, which is commonly used to activate carboxylic groups in an ester-modification or an amide-modification reaction in the field of organic synthetic chemistry.

The mixed acid anhydride of carboxylic acid of the formula [II] can be obtained by reacting carboxylic acid of the formula [II] with an alkyl chlorocarbonate such as an ethyl chlorocarbonate; or an aliphatic carboxylic acid chloride such as acetyl chloride or pivaloyl chloride in accordance with a conventional method. The active ester can be obtained, in accordance with a conventional method, by reacting carboxylic acid of the formula [II] with an N-hydroxy compound such as N-hydroxysuccinimide, N-hydroxyphthalimide or 1-hydroxybenzotriazole; or a phenol compound such as 4-nitrophenol, 2,4-dinitrophenol, 2,4,5-trichlorophenol or pentachlorophenol, in the presence of a condensing agent such as N,N'-dicyclohexylcarbodiimide, 1-ethyl-3-(3-dimethylaminopropyl)carbodiimide, diphenylphosphorylazide or dipyridyldisulfide-triphenylphosphine. The active amide can be obtained, in accordance with a conventional method, by reacting carboxylic acid of the formula [II] with e.g. 1,1'-carbonyldiimidazole or 1,1'-carbonylbis(2-methylimidazole).

The condensing reaction of the reactive derivative of carboxylic acid of the formula [II] with the compound of the formula [III] or [IV] is carried out preferably in an inert solvent. The inert organic solvent may, for example, be diethyl ether, tetrahydrofuran, N,N-dimethylformamide, dioxane, benzene, toluene, chlorobenzene, methylene chloride, chloroform, carbon tetrachloride, dichloroethane or trichloroethylene, or a mixture of the solvents. Particularly, diethyl ether, tetrahydrofuran, N,N-dimethylformamide and dioxane are preferred.

The reaction temperature is usually from −70° C. to the boiling point of the solvent to be used, preferably within a range of from −20° C. to 100° C.

The amount of the compound of the formula [III] or [IV] to the reactive derivative of carboxylic acid of the formula [II] is not strictly limited, and it can be varied depending upon the type of the reactive derivative. However, the amount of the compound of the formula [III] or [IV] is usually from 1 to 5 mol, preferably from 1 to 2 mol per mol of the reactive derivative of carboxylic acid of the formula [II].

In the case where $R^5$ is a protecting group, the protecting group may, for example, be an aralkyl group such as a benzyl group, a p-methoxybenzyl group, a p-nitrobenzyl group, a benzhydryl group or trityl group; a lower alkanoyl group such as a formyl group, an acetyl group or a propionyl group; an arylalkanoyl group such as a phenylacetyl group or a phenoxyacetyl group; a lower alkoxycarbonyl group such as a methoxycarbonyl group, an ethoxycarbonyl group or a t-butoxycarbonyl group; an alkenyloxycarbonyl group such as a 2-propenyloxycarbonyl group; an aralkyloxycarbonyl group such as a benzyloxycarbonyl group or a p-nitrobenzyloxycarbonyl group; or a lower alkylsilyl group such as a trimethylsilyl group or a t-butyldimethylsilyl group. Particularly, a t-butoxycarbonyl group and a benzyloxycarbonyl group are preferred.

When $R^5$ in the formula [Va] or [Vb] is the same as $R^3$, the compound of the present invention can be obtained directly by the above condensing reaction.

When $R^5$ in the formula [Va] or [Vb] is a protecting group, the protecting group is removed from the compound [Va] or [Vb], followed by reacting the compound [VI], or reductive alkylation by using the compound [VII] and a reducing agent is conducted, to obtain the compound of the present invention.

Removal of the protecting group can be conducted in accordance with a known method, such as a method disclosed in Protective Groups in Organic Synthesis, T. W. Greene, John Wiley & Sons (1981) or methods similar thereto. For example, it can be conducted by solvolysis employing an acid or a base, by chemical reduction employing a metal hydride complex or by catalytic reduction employing e.g. palladium—carbon catalyst or Raney nickel catalyst.

"A leaving group" represented as L may, for example, be a halogen atom such as a chlorine atom, a bromine atom or an iodine atom; an alkylsulfonyloxy group or an arylsulfonyloxy group such as a methanesulfonyloxy group or a p-toluenesulfonyloxy group.

The reaction of the compound obtained by removing a protecting group from the compound of the formula [Va] or [Vb] with the compound of the formula [VI] is conducted usually by using almost same mol of them or using them with a small excess of one to the other (for example, from 1 to 1.3 mol of the compound of the formula [VI] per mol of the compound obtained by removing a protecting group from the compound of the formula [Va] or [Vb]) in a suitable solvent. However, as the case requires, it can be conducted by using them with a large excess of one to the other. Further, as the case requires, a suitable base or reaction promotor can be used.

The solvent may, for example, be an ether such as diethyl ether, tetrahydrofuran or dioxane; an aromatic hydrocarbon such as benzene, toluene, chlorobenzene or xylene; an aprotic polar solvent such as dimethyl sulfoxide, N,N-dimethylformamide or acetonitrile, or mixed solvent of them.

The base to be used may, for example, be an alkali metal bicarbonate such as sodium hydrogencarbonate or potassium hydrogencarbonate; an alkali metal carbonate such as sodium carbonate or potassium carbonate; a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU) or 1,5-diazabicyclo[4.3.0]non-5-ene (DBN); or an aromatic amine such as pyridine, 4-dimethylaminopyridine, picoline, lutidine, quinoline or isoquinoline. Particularly, N,N-diisopropylethylamine and triethylamine are preferred.

As the reaction promotor to be used in the reaction, an alkali metal iodide such as lithium iodide, sodium iodide or potassium iodide, may be mentioned. Particularly, potassium iodide is preferred.

The reaction temperature is usually from about 0° C. to the boiling point of the solvent, and the reaction time is usually from 10 minutes to 48 hours. However, they may be varied, as the case required.

The reductive alkylation reaction of the compound obtained by removing a protecting group from the compound of the formula [Va] or [Vb] with the aldehyde of the formula [VII] is usually conducted in an inert solvent which does not deteriorate the reaction. The inert solvent may, for example, be an alcohol such as methanol or ethanol; an ether such as diethyl ether, tetrahydrofuran or dioxane; an aromatic hydrocarbon such as benzene or toluene, or a mixed solvent of them. Particularly, methanol, ethanol, tetrahydrofuran and toluene are preferred.

The reaction temperature is usually from about −30° C. to about 200° C., preferably from about 0° C. to about 100° C. The reaction time is usually from 10 minutes to 7 days, preferably from 10 minutes to 24 hours.

It is preferred to conduct the reductive alkylation reaction under weak acid condition wherein a Schiff base is likely to form. The acid used to adjust pH may, for example, be p-toluenesulfonic acid, hydrochloric acid, acetic acid or trifluoroacetic acid.

The reductive alkylation can be conducted by employing a metal hydride complex such as sodium borohydride, sodium cyanoborohydride, lithium aluminum hydride or sodium triacetoxyborohydride, or by catalytic reduction employing e.g. palladium—carbon catalyst or Raney nickel catalyst. It is preferred to conduct the reaction by employing a metal hydride complex such as sodium borohydride or sodium cyanoborohydride. Particularly, in the case where the reduction reaction is conducted under weak acid condition wherein a Schiff base is likely to form, it is preferred to use e.g. sodium cyanoborohydride which is relatively stable under acidic condition.

In the case where a metal hydride complex is used as a reducing agent, the amount of the reducing agent is usually from 1 mol to an excess molar amount, preferably from 1 to 10 mol per mol of the compound of the formula [XI].

In the case where at least one of $R^1$ and $R^2$ is a halogen atom, a lower alkoxycarbonyl group or an aralkyloxycarbonyl group, the halogen atom is reduced to a hydrogen atom, or in the case of a lower alkoxycarbonyl group or an aralkyloxycarbonyl group, it may be converted to a carbamoyl group, a lower alkylaminocarbonyl group, a di-lower alkylaminocarbonyl group, a lower alkoxycarbonyl(lower) alkylaminocarbonyl group, an aralkyloxycarbonyl(lower) alkylaminocarbonyl group, an aralkylaminocarbonyl group, a diaralkylaminocarbonyl group or a heteroaryl(lower)alkylaminocarbonyl group. The reaction of reducing a halogen atom to a hydrogen atom can be conducted by conventional catalytic reduction. Converting a lower alkoxycarbonyl group or an aralkyloxycarbonyl group to a carbamoyl group, a lower alkylaminocarbonyl group or a di lower alkylaminocarbonyl group, can be conducted by directly reacting with a corresponding amine compound, or converting to a carboxy group and then condensing with a corresponding amine compound by a conventional method.

Route 2

The reaction of the compound [VIII] with a phosgene or carbonyldiimidazole (CDI) can be conducted in a suitable solvent. A phosgene means not only phosgene itself but also diphosgene or triphosgene, and it is possible to suitably select among them depending upon the reaction condition. The solvent to be used may, for example, be chloroform, methylene chloride, toluene, xylene, diethyl ether, tetrahydrofuran, dioxane or dimethylformamide.

The reaction temperature is usually from $-10°$ C. to the boiling point of the solvent, but as the case requires, it may be higher or lower. The reaction time is usually from 30 minutes to one day, but as the case requires, it may be longer or shorter.

The compound produced by the reaction of the compound [VIII] with a phosgene may be isolated, or may not be isolated as it is initially formed to react with the compound [III] or [IV].

Further, if necessary, as explained in Route 1, the converting reaction of a halogen atom to a hydrogen atom, or the converting reaction of a lower alkoxycarbonyl group or an aralkyloxycarbonyl group to a carbamoyl group, a lower alkylaminocarbonyl group or a di-lower alkylaminocarbonyl group can be conducted.

Route 3

Route 3 is a process of reacting a tertiary amine represented by e.g. the compound [Ia] with a compound represented by the formula [X] to produce a quaternary amine. Usually, it can be conducted by reacting e.g. the compound [Ia] with an excess amount of the compound [X]. The reaction temperature is usually from $10°$ C. to the boiling point of the compound [X], or the boiling point of the solvent if it is used. However, as the case requires, it may be higher or lower. The reaction time is usually from 30 minutes to one day, but as the case requires, it may be longer or shorter.

When making the tertiary amine to quaternary, in the case where $R^1$ or $R^2$ is a heteroaryl(lower)alkylaminocarbonyl group having a heteroaryl group containing at least one nitrogen atom, it is possible to make the nitrogen atom quaternary at the same time.

The compounds produced by the above Route can be isolated and purified by a conventional method in the field of organic chemistry, such as extraction, recrystallization or chromatography.

Pharmacological Activity

Inhibitory activities against binding to the chemokine receptors, activities against intracellular cyclic AMP concentration and CCR3 antagonist activities of the compounds of the present invention are shown hereinafter.

(1) Test in Inhibitory Activities Against Binding to the Chemokine Receptor cDNAs which code human chemokine receptor CCR1 was subcloned to Hind III/Xba I part of the expression vector pRc/CMV (Invitrogen) to prepare pRc/CMV CCR1. Then, pRc/CMV CCR1 was transfected to CHO cells by using lipofectamine (GIBCO) to obtain a stable cell strain resistant against 0.5 mg/ml of G418.

The stable cell strain, 50 pM[$^{125}$I]MIP-1 alpha (2000 Ci/mmol, manufactured by New England Nuclear) and a test compound were suspended in 0.2 ml of Krebs-Ringer/0.1% bovine serum albumin/0.1% glucose (pH 7.4), and incubated for 90 minutes at a temperature of $37°$ C. Then, it was subjected to filtration by means of a glass filter GF/C which was preliminarily impregnated in 1% of polyethyleneimine, and washed with 1 ml of Krebs-Ringer/0.1% bovine serum albumin/0.1% glucose (pH 7.4), whereby radio activity on the glass filter was measured. The binding affinity to the chemokine receptors CCR1 was shown as a 50% inhibitory concentration (IC$_{50}$ value) of the compound of the present invention against [$^{125}$I]MIP-1 alpha binding. The IC$_{50}$ value of the compound obtained in Example 12 was 5.2 nM, the IC$_{50}$ value of the compound obtained in Example 22 was 3.9 nM, the IC$_{50}$ value of the compound obtained in Example 26 (named cis for convenience) was 1.9 nM, the IC$_{50}$ value of the compound obtained in Example 61 (named cis for convenience) was 1.8 nM, and the IC$_{50}$ value of the compound obtained in Example 62 (named cis for convenience) was 1.8 nM.

Further, an expression vector of a gene which codes chemokine receptor CCR3 was transfected to CHO cell by using lipofectamine to obtain a stable cell strain resistant against 0.5 mg/ml of G418. The stable cell strain, 50 pM[$^{125}$I]Eotaxin (2000 Ci/mmol, manufactured by Amersham) and a test compound were suspended in 0.2 ml of Krebs-Ringer/0.1% bovine serum albumin/0.1% glucose (pH 7.4) and incubated for 90 minutes at a temperature of $37°$ C. Then, it was subjected to filtration by means of a glass filter GF/C which was preliminarily impregnated in 1% polyethyleneimine, and washed with 1 ml of Krebs-Ringer/ 0.1% bovine serum albumin/0.1% glucose (pH 7.4), whereby radio activity on the glass filter was measured. The binding affinity to the chemokine receptors CCR3 was shown as a 50% inhibitory concentration (IC$_{50}$ value) of the compounds of the present invention against [$^{125}$I]Eotaxin binding. The IC$_{50}$ value of the compound obtained in Example 12 was 40 nM, the IC$_{50}$ of the compound obtained in Example 22 was 13 nM, the IC$_{50}$ of the compound obtained in Example 26 (named cis for convenience) was 2.7 nM, the IC$_{50}$ of the compound obtained in Example 61 (named cis for convenience) was 1.7 nM, and the IC$_{50}$ of the compound obtained in Example 62 (named cis for convenience) was 0.74 nM.

(2) Activities to Intracellular Cyclic AMP Concentration

By using CHO cells which stably express the chemokine receptor CCR1, the activity of the test compounds to intracellular cyclic AMP concentration had been studied.

The CHO cells was suspended in Locke's solution (pH 7.4:154 mM of sodium chloride, 5.6 mM of potassium chloride, 2 mM of calcium chloride, 1 mM of magnesium chloride, 0.1% glucose, 10 mM of Hepes and 0.3 mM of isobutylmethylxanthine), and preliminarily incubated at a temperature of $37°$ C. for 5 minutes, and 100 nM of hMIP-1 alpha and 0.01 mM of Forskolin were added thereto. The reaction was kept for 10 minutes and terminated by adding trichloroacetic acid. The reaction mixture was centrifuged at 15000 rpm for 5 minutes and supernatant was obtained. Trichloroacetic acid in the supernatant was removed by extraction with diethyl ether, and the supernatant was evaporated to dryness by centrifugal evaporator. The cyclic AMP concentration in the sample thus obtained was measured by cyclic AMP kit (produced by Amersham). The activity of test compounds to the cyclic AMP concentration was obtained by studying antagonism against hMIP-1 alpha by adding 0.01 mM of the test compounds 5 minutes before adding 100 nM of hMIP-1 alpha. The results are shown in Table 1.

TABLE 1

| Reaction conditions | cAMP concentration (pmol/10⁶ cells) |
|---|---|
| Forskolin solely | 67.8 +/− 8.4 |
| Forskolin + hMIP − 1 alpha | 47.7 +/− 4.2 |
| Forskolin + hMIP − 1 alpha + compound obtained in Example 12 | 81.6 +/− 4.2 |

As shown in Table 1, the compound of the present invention was found to antagonize the suppressing effect of MIP-1 alpha against Forskolin-induced intracellular cyclic AMP concentration.

(3) CCR3 Antagonist Activities

By using human eosinophil which stably express CCR3, the activity of the compounds of the present invention to intracellular calcium concentration was measured by the following method. 4 mM of Fura2 acetoxymethyl ester (produced by Dojin Kagaku Laboratories) was added to eosinophils and incubated for 30 minutes at a temperature of 37° C. Then, the mixture was excited by irradiation with light at 340 nm and 380 nm, fluorescence at 500 nm was measured, 340/380 ratio was monitored, thereby intracellular calcium concentration was calculated. As an agonist, CCR3 specific chemokine Eotaxin (10 nM) was used, and antagonist activity was obtained as an inhibitory ratio (%) of increase in the concentration of intracellular calcium when eosinophils were treated with 41 nM of the compounds of the present invention 5 minutes before the agonist stimulation. The inhibitory ratio of the compound obtained in Example 26 (named cis for convenience) was 51% and the inhibitory ratio of the compound obtained in Example 59 (named cis for convenience) was 97%.

To use the compounds of the present invention for practical use to treat or prevent diseases as mentioned above, they may be formulated into various formulations by adding pharmaceutically acceptable additives to meet the type of administration, in accordance with a conventional method. As such additives, various additives which are commonly used in the field of drug formulations, may be used, including, for example, gelatin, lactose, sucrose, titanium oxide, starch, crystalline cellulose, hydroxypropylmethylcellulose, carboxymethylcellulose, corn starch, microcrystalline wax, white petrolatum, magnesium metasilicate aluminate, anhydrous calcium phosphate, citric acid, trisodium citrate, hydroxypropylcellulose, sorbitol, sorbitan fatty acid ester, polysorbate, sucrose fatty acid ester, polyoxyethylene, hardened castor oil, polyvinylpyrrolidone, magnesium stearate, light silicic anhydride, talc, vegetable oil, benzyl alcohol, gum arabic, propylene glycol, polyalkylene glycol, cyclodextrin and hydroxypropylcyclodextrin.

A drug formulation to be formulated by using such additives, may, for example, be a solid formulation such as a tablet, a capsule, a granule, a powder or a suppository; or a liquid formulation such as a syrup, an elixir or an injecting drug. These formulations can be prepared in accordance with a conventional method commonly employed in the field of drug formulations. The liquid formulation may be of the type which is to be dissolved or suspended in water or in other suitable medium at the time of its use. Particularly, the injection drug may be dissolved or suspended preliminarily in a physiological saline or in a glucose solution, or may be a form of a powder which is to be dissolved or suspended in a physiological saline or in a glucose solution at the time of its use, and a buffering agent or a preserving agent may further be added.

These formulations may contain the compound of the present invention in a proportion of from 1.0 to 100 wt %, preferably from 1.0 to 60 wt % of the total amount of the drug. These formulations may further contain other therapeutically effective compounds.

When the compound of the present invention is used as an antiallergic, its dose and the frequency of administration vary depending upon the sex, the age, the body weight, the diseased degree of the patient, and the type and the range of the intended treating effects. However, in the case of an oral administration, it is preferred to administer from 0.1 to 100 mg/kg per day for an adult all at once or in a few times in a divided fashion. In the case of parenteral administration, it is preferred to administer from 0.001 to 10 mg/kg per day for an adult all at once or in a few times in a divided fashion.

Now, the present invention will be described in further detail with reference to Examples. However, the present invention is by no means restricted by such Examples.

EXAMPLE 1

Synthesis of N-[1-(cyclooctylmethyl)piperidin-4-yl] xanthene-9-carboxamide

Step 1. Synthesis of N-(1-t-butoxycarbonylpiperidin-4-yl) xanthene-9-carboxamide 4.71 g of 4-amino-1-t-butoxycarbonylpiperidine hydrochloride and 4.50 g of xanthene-9-carboxylic acid were suspended in 150 ml of anhydrous N,N-dimethylformamide, and 5.5 ml of triethylamine was added thereto. The mixture was cooled in ice and 5.73 g of 1-ethyl-3-(3-dimethylaminopropyl)carbodiimide hydrochloride (hereinafter referred to as EDCI.HCl) and 4.04 g of 1-hydroxybenzotriazole were successively added thereto. The temperature was raised to room temperature immediately, and the reaction solution was stirred for 12 hours. After the reaction solution was cooled to 0° C., 80 ml of water was added thereto, followed by extraction with ethyl acetate. The organic layer was washed with 10% citric acid solution, saturated aqueous sodium bicarbonate, water and saturated aqueous sodium chloride, followed by drying over anhydrous sodium sulfate. The solvent was distilled off under reduced pressure, and 7.78 g of the title compound as a white solid was obtained.

Step 2. Synthesis of N-(piperidin-4-yl)xanthene-9-carboxamide hydrochloride 70 ml of 10% HCl-methanol solution was added to 40 ml of methanol suspension having 7.78 g of N-(1-t-butoxycarbonylpiperidin-4-yl)xanthene-9-carboxamide, followed by stirring for 17 hours. The solvent was distilled off under reduced pressure, the obtained residue was washed with ethyl acetate, and 6.10 g of the title compound as a blue-green solid was obtained.

Step 3. Synthesis of N-[1-(cyclooctylmethyl)piperidin-4-yl] xanthene-9-carboxamide 1.16 g of N-(piperidin-4-yl)xanthene-9-carboxamide hydrochloride and 586 mg of cyclooctanecarbaldehyde were suspended in 60 ml of tetrahydrofuran at room temperature, and 1.60 g of sodium triacetoxyborohydride was added thereto, followed by stirring for 12 hours at the same temperature. Saturated aqueous sodium bicarbonate was added to the reaction solution, followed by extraction with ethyl acetate. The organic layer was washed with saturated aqueous sodium chloride, followed by drying over anhydrous sodium sulfate. The solvent was distilled off under reduced pressure, the obtained residue was purified by silica gel column chromatography (developing solvent: chloroform—chloroform/methanol=50/1), and 660 mg of the title compound as a white solid was obtained.

$^1$H-NMR(CDCl$_3$, δ ppm):1.11–1.74(19H, m), 1.89–1.97 (4H, m), 2.54–2.58(2H, m), 3.64–3.66(1H, m), 4.84(1H, s), 5.10(1H, d, J=8.1 Hz), 7.08–7.14(4H, m), 7.26–7.33(2H, m), 7.37–7.40(2H, m).

FAB-MS(m/e, as (C$_{28}$H$_{36}$O$_2$N$_2$+H)$^+$):433

EXAMPLE 2

Synthesis of N-[1-(cyclooctylethyl)piperidin-4-yl] xanthene-9-carboxamide

The title compound was synthesized in the same manner as in Step 3 of Example 1 by using cyclooctaneacetaldehyde.

$^1$H-NMR(CDCl$_3$, δ ppm):1.17–1.59(19H, m), 1.71–1.78 (2H, m), 1.95–2.03(2H, m), 2.22–2.27(2H, m), 2.59–2.66 (2H, m), 3.63–3.69(1H, m), 4.84(1H, s), 5.10(1H, d, J=7.6 Hz), 7.08–7.14(4H, m), 7.26–7.39(4H, m).

FAB-MS(m/e, as (C$_{29}$H$_{38}$O$_2$N$_2$+H)$^+$):447

EXAMPLE 3

Synthesis of N-[1-(cyclooctylpropyl)piperidin-4-yl] xanthene-9-carboxamide

The title compound was synthesized in the same manner as in Step 3 of Example 1 by using cyclooctanepropionaldehyde.

$^1$H-NMR(CDCl$_3$, δ ppm):1.07–1.85(23H, m), 2.02–2.14 (2H, m), 2.26–2.31(2H, m), 2.68–2.76(2H, m), 3.63–3.72 (1H, m), 4.85(1H, s), 5.21(1H, d, J=6.4 Hz), 7.08–7.15(4H, m), 7.28–7.35(2H, m), 7.36–7.39(2H, m).

FAB-MS(m/e, as (C$_{30}$H$_{40}$O$_2$N$_2$+H)$^+$):461

EXAMPLE 4

Synthesis of N-[1-(cyclononylmethyl)piperidin-4-yl] xanthene-9-carboxamide

The title compound was synthesized in the same manner as in Step 3 of Example 1 by using cyclononanecarbaldehyde.

$^1$H-NMR(CDCl$_3$, δ ppm):1.10–1.80(21H, m), 1.85–2.05 (4H, m), 2.48–2.62(2H, m), 3.55–3.75(1H, m), 4.84(1H, s), 5.10(1H, d, J=7.5 Hz), 7.05–7.45(8H, m).

FAB-MS(m/e, as (C$_{29}$H$_{38}$O$_2$N$_2$+H)$^+$):447

EXAMPLE 5

Synthesis of N-[1-(cyclohexylmethyl)piperidin-4-yl] xanthene-9-carboxamide

The title compound was synthesized in the same manner as in Step 3 of Example 1 by using cyclohexanecarbaldehyde.

$^1$H-NMR(CDCl$_3$, δ ppm):0.77–0.84(2H, m), 1.12–1.26 (4H, m), 1.34–1.39(1H, m), 1.57–1.75(10H, m), 1.89–1.96 (2H, m), 2.51–2.56(2H, m), 3.63–3.68(1H, m), 4.84(1H, s), 5.08(1H, d, J=5.9 Hz), 7.08–7.14(4H, m), 7.25–7.31(2H, m), 7.36–7.40(2H, m).

FAB-MS(m/e, as (C$_{26}$H$_{32}$O$_2$N$_2$+H)$^+$):405

EXAMPLE 6

Synthesis of N-[(2-decalylmethylpiperidin-4-yl)] xanthene-9-carboxamide

The title compound was synthesized in the same manner as in Step 3 of Example 1 by using 2-decalincarbaldehyde.

$^1$H-NMR(CDCl$_3$, δ ppm):0.79–2.00(21H, m), 2.00–2.30 (4H, m), 2.65–2.95(2H, m), 3.65–3.80(1H, m), 4.85(1H, s), 5.25–5.41(1H, br. d), 7.05–7.40(8H, m).

FAB-MS(m/e, as (C$_{30}$H$_{38}$O$_2$N$_2$+H)$^+$):459

EXAMPLE 7

Synthesis of N-(1-hexylpiperidin-4-yl)xanthene-9-carboxamide 60 mg of potassium carbonate and 25 ml of iodohexane were successively added to 5.0 ml of acetonitrile suspension having 50 mg of N-(piperidin-4-yl)xanthene-9-carboxamide hydrochloride, followed by reflux under heating for 4 hours. After cooled to room temperature, water was added to the reaction solution, followed by extraction with ethyl acetate and drying over anhydrous magnesium sulfate. The solvent was distilled off under reduced pressure, the obtained residue was purified by preparative thin layer chromatography (Kieselgel™60F$_{254}$, Art5744 produced by Merck Co.: chloroform/methanol=10/1), and 35 mg of the title compound as a white solid was obtained.

$^1$H-NMR(CDCl$_3$, δ ppm):0.85(3H, t, J=7.0 Hz), 1.15–1.90(12H, m), 1.95–2.75(6H, m), 3.60–3.77(1H, m), 4.82(1H, s), 5.15(1H, d, J=5.7 Hz), 7.05–7.40(8H, m).

FAB-MS(m/e, as (C$_{25}$H$_{32}$O$_2$N$_2$+H)$^+$):393

EXAMPLE 8

Synthesis of N-[9-(cyclooctylmethyl)-9-azabicyclo [3.3.1]nonan-3-yl]xanthene-9-carboxamide Step 1. Synthesis of N-(9-t-butoxycarbonyl-9-azabicyclo [3.3.1]nonan-3-yl)xanthene-9-carboxamide 15 ml of anhydrous N,N-dimethylformamide suspension having 165 mg of 3-amino-9-t-butoxycarbonyl-9-azabicyclo [3.3.1]nonane and 155 mg of xanthene-9-carboxylic acid was cooled with ice, and 224 mg of EDCI.HCl and 157 mg of 1-hydroxybenzotriazole were successively added thereto. The temperature was raised to room temperature immediately, and the reaction mixture was stirred for 21 hours. 10 ml of water was added to the reaction solution, followed by extraction with diethyl ether. The organic layer was washed with 10% citric acid solution, saturated aqueous sodium bicarbonate, water and saturated aqueous sodium chloride, followed by drying over anhydrous sodium sulfate. The solvent was distilled off under reduced pressure, and 301 mg of the title compound as a white solid was obtained.

Step 2. Synthesis of N-(9-azabicyclo[3.3.1]nonan-3-yl) xanthene-9-carboxamide hydrochloride 10 ml of 10% HCl-methanol solution was added to 199 mg of N-(9-t-butoxycarbonyl-9-azabicyclo[3.3.1]nonan-3-yl)xanthene-9-carboxamide, followed by stirring for 21 hours. The solvent was distilled off under reduced pressure, the obtained residue was washed with ethyl acetate, and 166 mg of the title compound as a white solid was obtained.

Step 3. Synthesis of N-[9-(cyclooctylmethyl)-9-azabicyclo [3.3.1]nonan-3-yl]-xanthene-9-carboxamide 38.5 mg of N-(9-azabicyclo[3.3.1]nonan-3-yl)xanthene-9-carboxamide hydrochloride and 44.1 mg of cyclooctanecarbaldehyde were suspended in 3 ml of methanol at room temperature, and 1.60 g of sodium triacetoxyborohydride was added thereto, followed by stirring for 12 hours at the same temperature. Saturated aqueous sodium bicarbonate was added to the reaction solution, followed by extraction with ethyl acetate. The organic layer was washed with saturated aqueous sodium chloride and dried over anhydrous sodium sulfate. The solvent was distilled off under reduced pressure, the obtained residue was purified by preparative thin layer chromatography (Kieselgel™60F$_{254}$, Art5744 produced by Merck Co.: chloroform/methanol=19/1), and 9.0 mg of the title compound as a white solid was obtained.

$^1$H-NMR(CDCl$_3$, δ ppm):1.06–1.90(25H, m), 2.18–2.25 (2H, m), 2.69–2.74(2H, m), 4.52–4.57(1H, m), 4.85(1H, s), 4.99–5.03(1H, m), 7.03–7.14(4H, m), 7.22–7.39(4H, m).

FAB-MS(m/e, as (C$_{31}$H$_{40}$O$_2$N$_2$+H)$^+$):473

EXAMPLE 9

Synthesis of N-[1-(cyclooctylmethyl)piperidin-4-yl] phenoxazine-9-carboxamide

Step 1. Synthesis of 4-t-butoxycarbonylamino-1-cyclooctylmethylpiperidine 1.80 g of 4-t-butoxycarbonylaminopiperidine and 1.28 g of cyclooctanecarbaldehyde were dissolved in 80 ml of methanol at room temperature, and 0.55 ml of acetic acid and 6.23 g of sodium triacetoxyborohydride were successively added thereto, followed by stirring for 17 hours at the same temperature. Saturated aqueous sodium bicarbonate was added to the reaction solution, followed by extraction with ethyl acetate. The organic layer was washed with 10% citric acid solution, saturated aqueous sodium bicarbonate, water and saturated aqueous sodium chloride and dried over anhydrous sodium sulfate. The solvent was distilled off under reduced pressure, the obtained residue was purified by silica gel column chromatography (developing solvent: chloroform—chloroform/methanol=25/1), and 1.66 g of the title compound as a white solid was obtained.

Step 2. Synthesis of 4-amino-1-cyclooctylmethylpiperidine dihydrochloride 15 ml of 10% HCl-methanol solution and 15 ml of diethyl ether were added to 1.66 g of 4-t-butoxycarbonylamino-1-cyclooctylmethylpiperidine, followed by stirring for 18 hours. The solvent was distilled off under reduced pressure, the obtained residue was washed with diethyl ether, and 1.44 g of the title compound as a white solid was obtained.

Step 3. Synthesis of N-[1-(cyclooctylmethyl)piperidin-4-yl]-phenoxazine-9-carboxamide 50.3 mg of phenoxazine was dissolved in 3 ml of tetrahydrofuran at room temperature, and 0.15 ml of triethylamine and 86 mg of triphosgene were successively added thereto. After refluxed under heating for 30 minutes, 110 mg of 4-amino-1-cyclooctylmethylpiperidine dihydrochloride and 0.15 ml of triethylamine were added thereto, followed by reflux under heating for 2 hours. Water was added to the reaction solution, followed by extraction with ethyl acetate. The organic layer was washed with saturated aqueous sodium chloride, and dried over anhydrous sodium sulfate. The solvent was distilled off under reduced pressure, the obtained residue was purified by preparative thin layer chromatography (Kieselgel™60F$_{254}$, Art5744 produced by Merck Co.: chloroform/methanol=30/1), and 105 mg of the title compound as a yellow solid was obtained.

$^1$H-NMR(CDCl$_3$, δ ppm):1.11–1.75(17H, m), 1.92–1.97 (2H, m), 2.01–2.11(4H, m), 2.71–2.80(2H, m), 3.72–3.78 (1H, m), 5.25(1H, d, J=5.8 Hz), 7.04–7.17(6H, m), 7.50(2H, d, J=7.1 Hz).

FAB-MS (m/e, as (C$_{27}$H$_{35}$O$_2$N$_3$+H)$^+$):434

EXAMPLE 10

Synthesis of N-[1-(cyclooctylmethyl)piperidin-4-yl] phenothiazine-9-carboxamide

The title compound was synthesized in the same manner as in Step 3 of Example 10 by using phenothiazine.

$^1$H-NMR(CDCl$_3$, δ ppm):1.11–1.65(17H, m), 1.87–2.08 (6H, m), 2.62–2.72(2H, m), 3.67–3.73(1H, m), 4.85(1H, d, J=7.6 Hz), 7.12– 7.33(4H, m), 7.36–7.40(2H, m), 7.53–7.57 (2H, m).

FAB-MS (m/e, as (C$_{27}$H$_{35}$ON$_3$S+H)$^+$):450

EXAMPLE 11

Synthesis of 1-cyclooctylmethyl-1-methyl-4-(xanthene-9-carboxamido)piperidinium iodide 1 ml of methyl iodide was added to 9 mg of N-[1-(cyclooctylmethyl)piperidin-4-yl]xanthene-9-carboxamide, followed by stirring for 19 hours at room temperature. Methyl iodide was distilled off under reduced pressure, and 12 mg of the title compound as a pale yellow solid was obtained.

$^1$H-NMR(CDCl$_3$, δ ppm):1.37–1.81(19H, m), 1.86–2.04 (2H, m), 2.14–2.49(2H, m), 3.23(3H, s), 3.40–3.69(2H, m), 3.98–4.26(1H, m), 5.17&5.41(1H, s), 6.90–7.60(8H, m), 8.25–8.52(1H, m).

FAB-MS (m/e, as (C$_{29}$H$_{39}$O$_2$N$_2$I–I)$^+$):447

EXAMPLE 12

Synthesis of 1-cyclooctylmethyl-1-ethyl-4-(xanthene-9-carboxamido)piperidinium iodide The title compound was synthesized in the same manner as in Example 11 by using ethyl iodide.

$^1$H-NMR(CDCl$_3$, δ ppm):1.18–2.03(24H, m), 2.15–2.51 (2H, m), 3.05–3.79(4H, m), 3.85–4.30(1H, m), 5.18 & 5.42(1H, s), 6.80–7.60(8H, m), 8.33 & 8.55(1H, d, J=7.7 Hz).

FAB-MS (m/e, as (C$_{30}$H$_{41}$O$_2$N$_2$I–I)$^+$):461

EXAMPLE 13

Synthesis of 1-cyclooctylmethyl-1-propyl-4-(xanthene-9-carboxamido)piperidinium iodide The title compound was synthesized in the same manner as in Example 11 by using 1-iodopropane.

$^1$H-NMR(CD$_3$OD, δ ppm):1.03&1.05(3H, t, J=7.3 Hz), 1.30–2.20(21H, m), 3.05–3.65(8H, m), 3.85–3.98(1H, m), 4.56(1H, s), 7.06–7.45(8H, m).

FAB-MS (m/e, as (C$_{31}$H$_{43}$O$_2$N$_2$I–I)$^+$):475

EXAMPLE 14

Synthesis of 1-allyl-1-cyclooctylmethyl-4-(xanthene-9-carboxamido)piperidinium bromide The title compound was synthesized in the same manner as in Example 11 by using allyl bromide.

$^1$H-NMR(CDCl$_3$, δ ppm):1.22–2.41(19H, m), 3.00–4.05 (9H, m), 5.29 & 5.47(1H, s), 5.65–6.10(3H, m), 6.80–7.80 (8H, m), 9.15 & 9.52(1H, d, J=8.5 Hz).

FAB-MS (m/e, as (C$_{31}$H$_{41}$O$_2$N$_2$Br–Br)$^+$):473

EXAMPLE 15

Synthesis of 1-cyclononylmethyl-1-methyl-4-(xanthene-9-carboxamido)piperidinium iodide The title compound was synthesized in the same manner as in Example 11 by using N-[1-(cyclononylmethyl)piperidin-4-yl]xanthene-9-carboxamide.

$^1$H-NMR(CD$_3$OD, δ ppm):1.20–2.21(21H, m), 3.11(3H, s), 3.15–3.65(6H, m), 3.80–3.97(1H, m), 4.93&4.95(1H, s), 7.05–7.35(8H, m).

FAB-MS (m/e, as (C$_{30}$H$_{41}$O$_2$N$_2$I–I)$^+$):461

EXAMPLE 16

Synthesis of 1-(1-decalylmethyl)-1-methyl-4-(xanthene-9-carboxamido)piperidinium iodide The title compound was synthesized in the same manner as in Example 11 by using N-[1-(1-decalylmethyl)piperidin-4-yl]xanthene-9-carboxamide.

$^1$H-NMR(CD$_3$OD, δ ppm):0.80–2.23(21H, m), 3.06 & 3.08(3H, s), 3.15–3.65(6H, m), 3.80–4.00(1H, m), 4.92 & 4.98(1H, s), 7.03–7.36(8H, m).

FAB-MS (m/e, as (C$_{31}$H$_{41}$O$_2$N$_2$I–I)$^+$):473

EXAMPLE 17

Synthesis of 1-(2-decalylmethyl)-1-methyl-4-(xanthene-9-carboxamido)piperidinium iodide The title compound was synthesized in the same manner as in Example 11 by using N-[1-(2-decalylmethyl)piperidin-4-yl]xanthene-9-carboxamide.

$^1$H-NMR(CD$_3$OD, δ ppm):0.80–2.09(21H, m), 3.02–3.68 (9H, m), 3.81–3.98(1H, m), 4.94&4.99(1H, s), 7.03–7.38 (8H, m).

FAB-MS (m/e, as (C$_{31}$H$_{41}$O$_2$N$_2$I–I)$^+$):473

EXAMPLE 18

Synthesis of 1-hexyl-1-methyl-4-(xanthene-9-carboxamido)piperidinium iodide

The title compound was synthesized in the same manner as in Example 11 by using N-(1-hexylpiperidin-4-yl)xanthene-9-carboxamide.

$^1$H-NMR(CD$_3$OD, δ ppm):0.85–2.10(15H, m), 3.07 & 3.10(3H, s), 3.30–4.00(7H, m), 4.90–5.00(1H, m), 7.05–7.35(8H, m).

EXAMPLE 19

Synthesis of N-[1-(1-cyclohexylethyl)piperidin-4-yl]-xanthene-9-carboxamide

The title compound was synthesized in the same manner as in Example 7 by using 1-cyclohexylethyl p-toluenesulfonate.

$^1$H-NMR(CDCl$_3$, δ ppm):0.74–0.92(5H, m), 1.03–1.35 (6H, m), 1.51–1.86(6H, m), 2.01–2.21(3H, m), 2.33–2.57 (3H, m), 3.59–3.66(1H, m), 4.84(1H, s), 5.12–5.18(1H, m), 7.03–7.19(4H, m), 7.20–7.40(4H, m).

FAB-MS (m/e, as (C$_{27}$H$_{34}$O$_2$N$_2$+H)$^+$):419

EXAMPLE 20

Synthesis of N-[1-(cyclooctylmethyl)piperidin-4-yl]-2,7-dibromoxanthene-9-carboxamide The title compound was synthesized by using 2,7-dibromoxanthene-9-carboxyic acid instead of xanthene-9-carboxylic acid, and 1,1'-carbonyldiimidazole instead of EDCI.HCl and 1-hydroxybenzotriazole in Step 1 of Example 1.

$^1$H-NMR(CDCl$_3$, δ ppm):1.09–1.95(19H, m), 1.95–2.07 (4H, m), 2.55–2.69(2H, m), 3.60–3.78(1H, m), 4.73(1H, s), 5.12(1H, d, J=8.0 Hz), 7.01(2H, d, J=8.6 Hz), 7.41(2H, dd, J=2.3, 8.6 Hz), 7.50(2H, d, J=2.3 Hz).

FAB-MS (m/e, as (C$_{28}$H$_{34}$O$_2$N$_2$Br$_2$+H)$^+$):589, 591, 593

EXAMPLE 21

Synthesis of N-[1-(1-adamantylmethyl)piperidin-4-yl]-xanthene-9-carboxamide

The title compound was synthesized in the same manner as in Step 3 of Example 1 by using 1-adamantanecarbaldehyde.

$^1$H-NMR(CDCl$_3$, δ ppm):1.16–1.26(2H, m), 1.36–1.50 (6H, m), 1.56–1.74(8H, m), 1.82–1.89(5H, m), 2.16–2.23 (2H, m), 2.46–2.54(2H, m), 3.58–3.66(1H, m), 4.85(1H, s), 5.07–5.11(1H, m), 7.08–7.14(4H, m), 7.26–7.33(2H, m), 7.37–7.40(2H, m).

FAB-MS (m/e, as (C$_{30}$H$_{36}$O$_2$N$_2$+H)$^+$):457

EXAMPLE 22

Synthesis of 1-cyclooctylmethyl-1-methyl-4-(2,7-dibromoxanthene-9-carboxamido)piperidinium iodide The title compound was synthesized in the same manner as in Example 11 by using N-[1-(cyclooctylmethyl)piperidin-4-yl]-2,7-dibromoxanthene-9-carboxamide.

$^1$H-NMR(CD$_3$OD, δ ppm):1.24–2.25(19H, m), 3.10 & 3.12(3H, s), 3.20–3.65(6H, m), 3.80–3.96(1H, m), 4.88(1H, s), 7.05–7.55(6H, m).

FAB-MS(m/e, as (C$_{29}$H$_{37}$O$_2$N$_2$Br$_2$I–I)$^+$):603, 605, 607

EXAMPLE 23

Synthesis of 1-cyclooctylmethyl-1-butyl-4-(xanthene-9-carboxamido)piperidinium iodide The title compound was synthesized in the same manner as in Example 11 by using n-butyl iodide.

$^1$H-NMR((CD$_3$OD, δ ppm):1.01 & 1.04(3H, t, J=7.3 Hz), 1.09–2.09(23H, m), 3.14–3.68(8H, m), 3.85–4.00(1H, m), 4.94 & 4.97(1H, s), 7.15–7.40(8H, m).

FAB-MS (m/e, as (C$_{32}$H$_{45}$O$_2$N$_2$I–I)$^+$):489

EXAMPLE 24

Synthesis of 1-(1-adamantylmethyl)-1-methyl-4-(xanthene-9-carboxamido)piperidinium iodide The title compound was synthesized in the same manner as in Example 11 by using N-[1-(1-adamantylmethyl)piperidin-4-yl]-xanthene-9-carboxamide.

$^1$H-NMR((CD$_3$)$_2$SO, δ ppm):1.56–2.02(19H, m), 3.13 (3H, s), 3.21–3.78(6H, m), 3.60–3.81(1H, s), 4.90(1H, s), 7.04–7.32(8H, m), 8.43(1H, d, J=7.4 Hz).

FAB-MS (m/e, as (C$_{31}$H$_{39}$O$_2$N$_2$I–I)$^+$):471

EXAMPLE 25

Synthesis of 1-cyclooctylethyl-1-methyl-4-(xanthene-9-carboxamido)piperidinium iodide The title compound was synthesized in the same manner as in Example 11 by using N-[1-(cyclooctylethyl)piperidin-4-yl]-xanthene-9-carboxamide.

$^1$H-NMR(($CD_3$)$_2$SO, δ ppm):1.20–2.05(21H, m), 3.00 (3H, s), 3.21–3.55(6H, m), 3.67–3.85(1H, m), 4.92(1H, s), 7.00–7.35(8H, m), 8.40–8.50(1H, m).

FAB-MS (m/e, as ($C_{30}H_{41}O_2N_2I$–I)$^+$):461

EXAMPLE 26

Synthesis of cis*-1-cyclooctylmethyl-1-ethyl-4-(2,7-dibromoxanthene-9-carboxamido)piperidinium iodide and trans*-1-cyclooctylmethyl-1-ethyl-4-(2, 7-dibromoxanthene-9-carboxamido)piperidinium iodide (here, cis* and trans* are provisionally assigned as the stereostructures have not yet been determined. The same applies hereinafter.)

5 ml of iodoethane was added to 204 mg of N-[1-(cyclooctylmethyl)piperidin-4-yl]-2,7-dibromoxanthene-9-carboxamide, followed by stirring for 44 hours in oil bath of 95° C. The reaction solution was concentrated, the obtained residue was purified by silica gel column chromatography (developing solvent: chloroform/methanol=97/3-95/5-10/1). 175 mg of the title compound as a colorless solid, named cis form for convenience, which was the fraction eluting first in silica gel column chromatography, and 90 mg of the title compound as a colorless solid, named trans form for convenience, which was the fraction eluting later in silica gel column chromatography, were obtained.

cis*-1-cyclooctylmethyl-1-ethyl-4-(2,7-dibromoxanthene-9-carboxamido)piperidinium iodide $^1$H-NMR($CDCl_3$, δ ppm):1.36(3H, t, J=7.1 Hz), 1.38–1.82(14H, m), 1.95–2.16(3H, m), 2.31–2.50(2H, m), 3.21(2H, d, J=4.3 Hz), 3.54–3.69(2H, m), 3.82(2H, q, J=7.1 Hz)3.88–4.04(2H, m), 4.23–4.35(1H, m), 5.39(1H, s), 6.91 (2H, d, J=8.7 Hz), 7.31(2H, dd, J=2.4, 8.7 Hz), 7.55(2H, d, J=2.4 Hz), 8.88(1H, d, J=8.6 Hz).

FAB-MS(m/e, as ($C_{30}H_{39}O_2N_2Br_2I$–I)$^+$):617, 619, 621 trans*-1-cyclooctylmethyl-1-ethyl-4-(2,7-dibromoxanthene-9-carboxamido)piperidinium iodide $^1$H-NMR($CDCl_3$, δ ppm):1.29(3H, t, J=7.1 Hz), 1.38–2.25(19H, m), 3.36–3.52(2H, m), 3.43(2H, q, J=7.1 Hz), 3.58(2H, d, J=4.0 Hz), 4.20–4.41(3H, m), 5.57(1H, s), 6.92(2H, d, J=8.7 Hz), 7.30(2H, dd, J=2.3, 8.7 Hz), 7.61(2H, d, J=2.3 Hz), 9.12(1H, d, J=8.5 Hz).

FAB-MS (m/e, as ($C_{30}H_{39}O_2N_2Br_2I$–I)$^+$):617, 619, 621

EXAMPLE 27

Synthesis of 1-cyclooctylmethyl-1-propyl-4-(2,7-dibromoxanthene-9-carboxamido)piperidinium iodide The title compound was synthesized in the same manner as in Example 13 by using N-[1-(cyclooctylmethyl)piperidin-4-yl]-2,7-dibromoxanthene-9-carboxamide.

$^1$H-NMR($CDCl_3$, δ ppm):1.07 & 1.13(3H, t, J=7.1 Hz), 0.90–2.53(21H, m), 3.10–4.46(9H, m), 5.36 & 5.67(1H, s), 6.90&6.93(2H, d, J=8.7 Hz), 7.29 & 7.31(2H, dd, J=2.4, 8.7 Hz), 7.56&7.63(2H, d, J=2.4 Hz), 8.84 & 9.04(1H, d, J=8.4 Hz).

FAB-MS(m/e, as ($C_{31}H_{41}O_2N_2Br_2I$–I)$^+$):631, 633, 635

EXAMPLE 28

Synthesis of 1-cyclooctylmethyl-1-methyl-4-(2,7-divinylxanthene-9-carboxamido)piperidinium iodide Step 1. Synthesis of methyl 2,7-divinylxanthene-9-carboxylate Dioxane solution having 200 mg of methyl 2,7-dibromoxanthene-9-carboxylate, 0.45 ml of vinyltributyl tin and 35 mg of bis(triphenylphosphine)palladium(II) chloride was stirred for 3 hours in oil bath of 120° C. After cooled to room temperature, saturated aqueous sodium bicarbonate was added to reaction solution, followed by extraction with ethyl acetate. The organic layer was washed with 40% potassium fluoride solution and dried over anhydrous sodium sulfate. The solvent was distilled off under reduced pressure, the obtained residue was purified by silica gel column chromatography (developing solvent: hexane/ethyl acetate=19/1), and 92 mg of the title compound as a white amorphous was obtained.

Step 2. Synthesis of 2,7-divinylxanthene-9-carboxylic acid 0.2 ml of 4N sodium hydroxide was added to 0.5 ml THF-0.5 ml MeOH slution having 83 mg of methyl 2,7-divinylxanthene-9-carboxylate, followed by stirring for 14 hours at room temperature. The reaction solution was concentrated, and then diluted with water, followed by extraction with ethyl acetate. The aqueous layer was acidified with 1N hydrochlric acid, extracted with ethyl acetate, and dried over anhydrous magnesium sulfate. The solvent was distilled off under reduced pressure, and 62 mg of the title compound as a colorless solid was obtained.

Step 3. Synthesis of N-[1-(cyclooctylmethyl)piperidin-4-yl]-2,7-divinylxanthene-9-carboxamide The title compound was synthesized by using 2,7-divinylxanthene-9-carboxylic acid instead of xanthene-9-carboxylic acid in Step 1 of Example 1.

Step 4. Synthesis of 1-cyclooctylmethyl-1-methyl-4-(2,7-divinylxanthene-9-carboxamido)piperidinium iodide The title compound was synthesized in the same manner as in Example 20 by using N-[1-(cyclooctylmethyl)piperidin-4-yl]-2,7-divinylxanthene-9 -carboxamide.

$^1$H-NMR(($CD_3$)$_2$SO, δ ppm):1.19–2.20(19H, m), 3.03 (3H, s), 3.11–3.55(6H, m), 3.68–3.85(1H, m), 4.90(1H, s), 5.21(2H, d, J=11.0 Hz), 5.74(2H, d, J=17.7 Hz), 6.70(2H, dd, J=11.0, 17.7 Hz), 7.11(2H, d, J=8.5 Hz), 7.37(2H, d, J=2.0 Hz), 7.44(2H, dd, J=2.0, 8.5 Hz), 8.41&8.45(1H, d, J=7.9 Hz).

FAB-MS(m/e, as ($C_{33}H_{43}O_2N_2I$–I)$^+$):499

EXAMPLE 29

Synthesis of 1-cyclooctylmethyl-1-methyl-4-(2-bromoxanthene-9-carboxamido)piperidinium iodide Step 1. Synthesis of N-[1-(cyclooctylmethyl)piperidin-4-yl]-2-bromoxanthene-9-carboxamide The title compound was synthesized by using 2-bromoxanthene-9-carboxylic acid instead of xanthene-9-carboxylic acid in Step 1 of Example 1.

Step 2. Synthesis of 1-cyclooctylmethyl-1-methyl-4-(2-bromoxanthene-9-carboxamido)piperidinium iodide The title compound was synthesized in the same manner as in Example 11 by using N-[1-(cyclooctylmethyl)piperidin-4-yl]-2-bromoxanthene-9-carboxamide.

$^1$H-NMR(($CD_3$)$_2$SO, δ ppm):1.08–2.20(19H, m), 3.04 (3H, s), 3.11–3.56(6H, m), 3.64–3.85(1H, m), 4.93 & 4.95 (1H, s), 7.00–7.72(7H, m), 8.44 & 8.49(1H, d, J=7.3 Hz)

FAB-MS(m/e, as ($C_{29}H_{38}O_2N_2BrI$–I)$^{30}$):525, 527

EXAMPLE 30

Synthesis of 1-cyclooctylmethyl-1-methyl-4-(2,7-diethylxanthene-9-carboxamido)piperidinium iodide Step 1. Synthesis of N-[1-(cyclooctylmethyl)piperidin-4-yl]-2.7-diethylxanthene-9-carboxamide 33 mg of N-[1-(cyclooctylmethyl)piperidin-4-yl]-2,7-divinylxanthene-9-carboxamide was dissolved in 2 ml methanol-6 ml ethyl acetate, 20 mg of 10% palladium—carbon catalyst was added thereto, followed by catalytic reduction for 15 hours at room temperature under hydrogen normal pressure. The catalyst was removed by filtration, the filtrate was evaporated to dryness, and the obtained residue was purified by silica gel column chromatography (developing solvent: chloroform/methanol=97/3), and 22 mg of the title compound as colorless amorphous was obtained.

Step 2. Synthesis of 1-cyclooctylmethyl-1-methyl-4-(2,7-diethylxanthene-9-carboxamido)piperidinium iodide The title compound was synthesized in the same manner as in Example 11 by using N-[1-(cyclooctylmethyl)piperidin-4-yl]-2,7-diethylxanthene-9-carboxamide.

$^1$H-NMR(CDCl$_3$, δ ppm):1.20 & 1.18(6H, t, J=7.6 Hz), 1.38–2.52(19H, m), 2.59(4H, q, J=7.6 Hz), 3.24 & 2.99(3H, s), 3.15–3.99(6H, m), 4.08–4.23(1H, m), 5.04 & 5.24(1H, s), 6.90–7.34(6H, m), 8.08 & 8.31(1H, d, J=8.0 Hz).

FAB-MS (m/e, as $(C_{33}H_{47}O_2N_2I-I)^+$):503

EXAMPLE 31

Synthesis of 1-cyclooctylmethyl-1-methyl-4-(2,7-dichloroxanthene-9-carboxamido)piperidinium iodide Step 1. Synthesis of N-[1-(cyclooctylmethyl)piperidin-4-yl]-2,7-dichloroxanthene-9-carboxamide The title compound was synthesized by using 2,7-dichloroxanthene-9-carboxylic acid instead of xanthene-9-carboxylic acid in Step 1 of Example 1.

Step 2. Synthesis of 1-cyclooctylmethyl-1-methyl-4-(2,7-dichloroxanthene-9-carboxamido)piperidinium iodide The title compound was synthesized in the same manner as in Example 11 by using N-[1-(cyclooctylmethyl)piperidin-4-yl]-2,7-dichloroxanthene-9-carboxamide.

$^1$H-NMR((CD$_3$)$_2$SO, δ ppm):1.20–2.18(19H, m), 3.02 (3H, s), 3.11–3.53(6H, m), 3.65–3.83(1H, m), 4.91(1H, s), 7.16–7.47(6H, m), 8.41(1H, d, J=5.9 Hz).

FAB-MS(m/e, as $(C_{29}H_{37}O_2N_2Cl_2I-I)^+$):515

EXAMPLE 32

Synthesis of 1-cyclooctylmethyl-1-methyl-4-(thioxanthene-9-carboxamido)piperidinium iodide Step 1. Synthesis of N-[1-(cyclooctylmethyl)piperidin-4-yl]-thioxanthene-9-carboxamide The title compound was synthesized by using thioxanthene-9-carboxylic acid instead of xanthene-9-carboxylic acid in Step 1 of Example 1.

Step 2. Synthesis of 1-cyclooctylmethyl-1-methyl-4-(thioxanthene-9-carboxamido)piperidinium iodide The title compound was synthesized in the same manner as in Example 11 by using N-[1-(cyclooctylmethyl)piperidin-4-yl]-thioxanthene-9-carboxamide.

$^1$H-NMR((CD$_3$)$_2$SO, δ ppm):1.20–2.15(19H, m), 2.97 & 3.01(3H, s), 3.17–3.45(6H, m), 3.70–3.86(1H, m), 4.90 & 4.95(1H, s), 7.26–7.51(8H, m), 7.59&7.90(1H, d, J=6.5 Hz).

FAB-MS (m/e, as $(C_{29}H_{39}O_2N_2SI-I)^+$):463

EXAMPLE 33

Synthesis of 1-cyclooctylmethyl-1-methyl-4-(2,7-dimethylxanthene-9-carboxamido)piperidinium iodide Step 1. Synthesis of N-[1-(cyclooctylmethyl)piperidin-4-yl]-2,7-dimethylxanthene-9-carboxamide The title compound was synthesized by using 2,7-dimethylxanthene-9-carboxylic acid instead of xanthene-9-carboxylic acid in Step 1 of Example 1.

Step 2. Synthesis of 1-cyclooctylmethyl-1-methyl-4-(2,7-dimethylxanthene-9-carboxamido)piperidinium iodide The title compound was synthesized in the same manner as in Example 11 by using N-[1-(cyclooctylmethyl)piperidin-4-yl]-2,7-dimethylxanthene-9-carboxamide.

$^1$H-NMR((CD$_3$)$_2$SO, δ ppm): 1.15–2.20(19H, m), 2.29 (6H, s), 3.01(3H, s), 3.12–3.55(6H, m), 3.65–3.74(1H, m), 4.79(1H, s), 6.88–7.16(6H, m), 8.31 & 8.41(1H, d, J=7.5 Hz).

FAB-MS (m/e, as $(C_{31}H_{43}O_2N_2I-I)^+$):475

EXAMPLE 34

Synthesis of 1-cyclooctylmethyl-1-methyl-4-(3,6-dimethylxanthene-9-carboxamido)piperidinium iodide Step 1. Synthesis of 3,6-dimethylxanthene 4 ml of ethanol was added to 164 mg of 3,6-dimethylxanthone, followed by reflux under heating to dissolve it. 250 mg of metal sodium was added thereto, followed by stirring for 20 minutes at the same temperature. Water was added to the reaction solution, precipitated crystal was obtained by filtration, and 130 mg of the title compound as a colorless solid was obtained.

Step 2. Synthesis of 3,6-dimethylxanthene-9-carboxylic acid 0.74 ml of 1.68 M of n-butyllithium in hexane solution was added to 1 ml of THF having 130 mg of 3,6-dimethylxanthene, followed by stirring for 2 hours at room temperature. Dry ice was added to the reaction solution, and the temperature was raised to room temperature. The reaction solution was acidified with 1N hydrochloric acid, extracted with ethyl acetate, and dried over anhydrous magnesium sulfate. The solvent was distilled off under reduced pressure, the obtained residue was purified by preparative thin layer chromatography (Kieselgel™60F$_{254}$, Art5744 produced by Merck Co.: chloroform/methanol=15/2), and 46 mg of the title compound as a colorless solid was obtained.

Step 3. Synthesis of N-[1-(cyclooctylmethyl)piperidin-4-yl]-3,6-dimethylxanthene-9-carboxamide The title compound was synthesized by using 3,6-dimethylxanthene-9-carboxylic acid instead of xanthene-9-carboxylic acid in Step 1 of Example 1.

Step 4. Synthesis of 1-cyclooctylmethyl-1-methyl-4-(3,6-dimethylxanthene-9-carboxamido)piperidinium iodide The title compound was synthesized in the same manner as in Example 11 by using N-[1-(cyclooctylmethyl)piperidin-4-yl]-3,6-dimethylxanthene-9-carboxamide.

$^1$H-NMR((CD$_3$)SO, δ ppm):1.09–2.32(19H, m), 2.26(6H, s), 3.03(3H, s), 3.10–3.59(6H, m), 3.65–3.87(1H, m), 4.80 & 4.81(1H, s), 6.94–7.15(6H, m), 8.37 & 8.43(1H, d, J=7.3 Hz).

FAB-MS (m/e, as $(C_{31}H_{43}O_2N_2I-I)^+$):475

EXAMPLE 35

Synthesis of 1-cyclooctylmethyl-1-methyl-4-(3-methylxanthene-9-carboxamido)piperidinium iodide Step 1. Synthesis of 3-methylxanthene-9-carboxylic acid The title compound was synthesized in the same manner as in Steps 1 and 2 of Example 34.

Step 2. Synthesis of N-[1-(cyclooctylmethyl)piperidin-4-yl]-3-methylxanthene-9-carboxamide The title compound was synthesized by using 3-methylxanthene-9-carboxylic acid instead of xanthene-9-carboxylic acid in Step 1 of Example 1.

Step 3. Synthesis of 1-cyclooctylmethyl-1-methyl-4-(3-methylxanthene-9-carboxamido)piperidinium iodide The title compound was obtained in the same manner as in Example 11 by using N-[1-(cyclooctylmethyl)piperidin-4-yl]-3-methylxanthene-9-carboxamide.

$^1$H-NMR((CD$_3$)$_2$SO, δ ppm):1.20–2.00(19H, m), 2.29 (3H, s), 3.02(3H, s), 3.17–3.52(6H, m), 3.65–3.82(1H, m), 4.85(1H, s), 6.89–7.30(7H, m), 8.36 & 8.44(1H, d, J=7.3 Hz).

FAB-MS (m/e, as (C$_{30}$H$_{41}$O$_2$N$_2$I–I)$^+$):461

EXAMPLE 36

Synthesis of 1-cyclooctylmethyl-1-methyl-4-(3-methoxyxanthene-9-carboxamido)piperidinium iodide Step 1. Synthesis of 3-methoxyxanthene-9-carboxylic acid The title compound was synthesized in the same manner as in Steps 1 and 2 of Example 34.

Step 2. Synthesis of N-[1-(cyclooctylmethyl)piperidin-4-yl]-3-methoxyxanthene-9-carboxamide The title compound was synthesized by using 3-methoxyxanthene-9-carboxylic acid instead of xanthene-9-carboxylic acid in Step 1 of Example 1.

Step 3. Synthesis of 1-cyclooctylmethyl-1-methyl-4-(3-methoxyxanthene-9-carboxamido)piperidinium iodide The title compound was synthesized in the same manner as in Example 11 by using N-[1-(cyclooctylmethyl) piperidin-4-yl]-3-methoxyxanthene-9-carboxamide.

$^1$H-NMR((CD$_3$)$_2$SO, δ ppm):1.20–2.18(19H, m), 3.01 (3H, s), 3.18–3.50(6H, m), 3.76(3H, s), 3.52–3.82(1H, m), 4.82(1H, s), 6.67–7.32(7H, m), 8.33 & 8.41(1H, d, J=7.3 Hz).

FAB-MS (m/e, as (C$_{30}$H$_{41}$O$_3$N$_2$I–I)$^+$):477

EXAMPLE 37

Synthesis of 1-cyclooctylmethyl-1-methyl-4-(2,6-dimethoxyxanthene-9-carboxamido)piperidinium iodide Step 1. Synthesis of 2,6-dimethoxyxanthene-9-carboxylic acid The title compound was obtained in the same manner as in Steps 1 and 2 of Example 34.

Step 2. Synthesis of N-[1-(cyclooctylmethyl)piperidin-4-yl]-2,6-dimethoxyxanthene-9-carboxamide The title compound was synthesized by using 2,6-dimethoxyxanthene-9-carboxylic acid instead of xanthene-9-carboxylic acid in Step 1 of Example 1.

Step 3. Synthesis of 1-cyclooctylmethyl-1-methyl-4-(2,6-dimethoxyxanthene-9-carboxamido)piperidinium iodide The title compound was synthesized in the same manner as in Example 11 by using N-[1-(cyclooctylmethyl) piperidin-4-yl]-2,6-dimethoxyxanthene-9-carboxamide.

$^1$H-NMR((CD$_3$)$_2$SO, δ ppm):1.21–1.99(19H, m), 3.01 (3H, s), 3.19–3.45(6H, m), 3.54–3.85(1H, m), 3.73(3H, s), 3.75(3H, s), 4.78 (1H, s), 6.66–7.17(6H, m), 8.29 & 8.37 (1H, d, J=7.0 Hz).

FAB-MS (m/e as (C$_3$H$_{43}$O$_4$N$_2$I–I)$^+$):507

EXAMPLE 38

Synthesis of N-[1-(cyclooctylmethyl)piperidin-4-yl]-2-bromo-7-methoxycarbonylxanthene-9-carboxamide Step 1. Synthesis of 7-bromo-9-t-butoxycarbonylxanthene-2-carboxylic acid 20 ml of 1.63 M of n-butyllithium in hexane solution was added to 80 ml of anhydrous THF solution having 4.33 g of t-butyl 2,7-dibromoxanthene-9-carboxylate at a temperature of –78° C. 20 Minutes later, dry ice was added, and the temperature was raised to room temperature. 10% citric acid solution was added to the reaction solution, followed by extraction with ethyl acetate, and drying over anhydrous magnesium sulfate. The solvent was distilled off under reduced pressure, and 2.09 g of the title compound as a colorless solid was obtained.

Step 2. Synthesis of t-butyl 2-bromo-7-methoxycarbonylxanthene-9-carboxylate 50 ml of hexane solution having about 10% of trimethylsilyldiazomethane was added to 20 ml of methanol solution having 1.78 g of 7-bromo-9-t-butoxycarbonylxanthene-2-carboxylic acid, followed by stirring for 2 hours. The solvent was distilled off under reduced pressure, the obtained residue was purified by silica gel column chromatography (developing solvent: hexane/ethyl acetate=9/1), and 0.61 g of the title compound was obtained.

Step 3. Synthesis of 2-bromo-7-methoxycarbonylxanthene-9-carboxylic acid 3.0 ml of trifluoroacetic acid was added to 0.61 g of t-butyl 2-bromo-7-methoxycarbonylxanthene-9-carboxylate, followed by stirring for 30 minutes. Trifluoroacetic acid was distilled off under reduced pressure, and 0.50 g of the title compound as a colorless solid was obtained.

Step 4. Synthesis of N-[1-(cyclooctylmethyl)piperidin-4-yl]-2-bromo-7-methoxycarbonylxanthene-9-carboxamide The title compound was synthesized in the same manner as in Example 20.

$^1$H-NMR(CDCl$_3$, δ ppm):1.09–1.85(19H, m), 1.91–2.15 (4H, m), 2.55–2.73(2H, m), 3.60–3.78(1H, m), 3.91(3H, s), 4.80(1H, s), 5.14(1H, d, J=7.5 Hz), 7.04(1H, d, J=8.8 Hz), 7.17(1H, d, J=8.7 Hz), 7.42(1H, dd, J=2.4, 8.8 Hz), 7.54(1H, d, J=2.4 Hz), 8.00(1H, dd, J=2.0, 8.7 Hz), 8.07(1H, d, J=2.0 Hz).

FAB-MS(m/e, as (C$_{30}$H$_{37}$O$_4$N$_2$Br+H)$^+$):569, 571

EXAMPLE 39

Synthesis of 1-cyclooctylmethyl-1-methyl-4-(2-bromo-7-methoxycarbonylxanthene-9-carboxamido) piperidinium iodide The title compound was synthesized in the same manner as in Example 11 by using N-[1-(cyclooctylmethyl) piperidin-4-yl]-2-bromo-7-methoxycarbonylxanthene-9-carboxamide.

$^1$H-NMR((CD$_3$)$_2$SO, δ ppm):1.19–2.52(19H, m), 3.14&3.41(3H, s), 3.37(2H, d, J=4.0 Hz), 3.86(3H, s), 3.50–4.40(5H, m), 5.35 & 5.66(1H, s), 6.94 & 6.89(1H, d, J=8.7 Hz), 7.05 & 7.00(1H, d, J=8.6 Hz), 7.30(1H, dd, J=2.3, 8.7 Hz), 7.61 & 7.70(1H, d, J=2.3 Hz), 7.86 & 7.83(1H, dd, J=1.9, 8.6 Hz), 8.00 & 8.06(1H, d, J=1.9 Hz), 8.77 & 8.97(1H, d, J=8.4 Hz).

FAB-MS (m/e, as (C$_{31}$H$_{40}$O$_4$N$_2$BrI–I)$^+$):583, 585

EXAMPLE 40

Synthesis of N-[1-(cyclooctylmethyl)piperidin-4-yl]-2-methoxycarbonylxanthene-9-carboxamide Step 1. Synthesis of t-butyl 2-methoxycarbonylxanthene-9-carboxylate 1.25 g of t-butyl 2-bromo-7-methoxycarbonylxanthene-9-carboxylate was dissolved in 100 ml of ethyl acetate, 500 mg of 10% palladium—carbon catalyst was added thereto, followed by catalytic reduction for 11 hours at room temperature under hydrogen atmosphere. The catalyst was removed by filtration, the filtrate was distilled off under reduced pressure, and 0.39 g of the title compound as a colorless solid was obtained.

Step 2. Synthesis of 2-methoxycarbonylxanthene-9-carboxylic acid

The title compound was synthesized in the same manner as in Step 3 of Example 38.

Step 3. Synthesis of N-[1-(cyclooctylmethyl)piperidin-4-yl]-2-methoxycarbonylxanthene-9-carboxamide The title compound was synthesized in the same manner as in Example 20.

$^1$H-NMR(CDCl$_3$, δ ppm):1.08–1.85(19H, m), 1.85–2.14 (4H, m), 2.48–2.73(2H, m), 3.60–3.74(1H, m), 3.91(3H, s), 4.85(1H, s), 5.08–5.20(1H, m), 7.10–7.40(5H, m), 7.99(1H, dd, J=2.0, 8.6 Hz), 8.14(1H, d, J=2.0 Hz).

FAB-MS(m/e, as $(C_{30}H_{38}O_4N_2+H)^+$):491

EXAMPLE 41

Synthesis of 1-cyclooctylmethyl-1-methyl-4-(2-methoxycarbonylxanthene-9-carboxamido) piperidinium iodide The title compound was synthesized in the same manner as in Example 11 by using N-[1-(cyclooctylmethyl) piperidin-4-yl]-2-methoxycarbonylxanthene-9-carboxamide.

$^1$H-NMR(CDCl$_3$, δ ppm):1.15–2.50(19H, m), 3.34&3.09 (3H, s), 3.30(2H, d, J=3.6Hz), 3.49–3.91(4H, m), 3.86(3H, s), 4.09–4.30(1H, m), 5.27&5.55(1H, s), 6.90–7.35(4H, m), 7.50–7.65(1H, m), 7.88 & 8.86(1H, dd, J=2.0, 8.6 Hz), 7.98 & 8.02(1H, d, J=2.0 Hz), 8.69 & 8.89(1H, d, J=8.0 Hz).

FAB-MS (m/e, as $(C_{31}H_{41}O_4N_2I-I)^+$):505

EXAMPLE 42

Synthesis of N-[1-(cyclooctylmethyl)piperidin-4-yl]-2-formyl-7-methoxycarbonylxanthene-9-carboxamide Step 1. Synthesis of t-butyl 2-methoxcarbonyl-7-vinylxanthene-9-carboxylate The title compound was synthesized in the same manner as in Step 1 of Example 28.

Step 2. Synthesis of t-butyl 2-(1,2-dihydroxyethyl)-7-methoxycarbonylxanthene-9-carboxylate 1.0 ml of 4% aqueous osmium tetraoxide solution was added to 1.0 ml t-butanol-5.0 ml acetone solution having 250 mg of t-butyl 2-methoxycarbonyl-7-vinylxanthene-9-carboxylate and 140 mg of N-methylmorpholine N-oxide, followed by stirring for 3 hours at room temperature. Aqueous sodium sulfite solution was added to the reaction solution, followed by stirring for 30 minutes. The reaction mixture was extracted with ethyl acetate, and dried over anhydrous magnesium sulfate. The solvent was distilled off under reduced pressure, the obtained residue was purified by silica gel column chromatography (developing solvent: hexane/ethyl acetate=3/7), and 162 mg of the title compound was obtained.

Step 3. Synthesis of t-butyl 2-formyl-7-methoxycarbonylxanthene-9-carboxylate 250 mg of sodium periodate was added to 5 ml ether-5 ml water-5 ml methanol suspension having 160 mg of t-butyl 2-(1,2-dihydroxyethyl)-7-methoxycarbonylxanthene-9-carboxylate, followed by stirring for 10 hours at room temperature. Saturated aqueous sodium chloride was added to the reaction solution, followed by extraction with ethyl acetate, and drying over anhydrous magnesium sulfate. The solvent was distilled off under reduced pressure, and 142 mg of the title compound as the colorless solid was obtained.

Step 4. Synthesis of 2-formyl-7-methoxycarbonylxanthene-9-carboxylic acid

The title compound was synthesized in the same manner as in Step 3 of Example 38.

Step 5. Synthesis of N-[1-(cyclooctylmethyl)piperidin-4-yl]-2-formyl-7-methoxycarbonylxanthene-9-carboxamide The title compound was synthesized in the same manner as in Example 20.

$^1$H-NMR(CDCl$_3$, δ ppm):1.05–2.23(23H, m), 2.56–2.75 (2H, m), 3.58–3.80(1H, m), 3.92(3H, s), 4.90(1H, s), 5.52 (1H, d, J=7.7 Hz), 7.20 (1H, d, J=8.5 Hz), 7.26(1H, d, J=8.5 Hz), 7.85(1H, dd, J=2.0, 8.5 Hz), 7.93(1H, d, J=2.0 Hz), 8.01(1H, dd, J=2.1, 8.5 Hz), 8.05(1H, d, J=2.1 Hz), 9.93(1H, s).

FAB-MS (m/e, as $(C_{31}H_{38}O_5N_2+H)^+$):519

EXAMPLE 43

Synthesis of 1-cyclooctylmethyl-1-methyl-4-(2-formyl-7-methoxycarbonylxanthene-9-carboxamido) piperidinium iodide The title compound was synthesized in the same manner as in Example 11 by using N-[1-(cyclooctylmethyl) piperidin-4-yl]-2-formyl-7-methoxycarbonylxanthene-9-carboxamide.

$^1$H-NMR(CDCl$_3$, δ ppm):1.30–2.55(19H, m), 3.15&3.50 (3H, s), 3.30–4.50(7H, m), 3.88(3H, s), 5.52 & 5.82(1H, s), 7.09 & 7.14(1H, d, J=8.6 Hz), 7.14 & 7.20(1H, d, J=8.6 Hz), 7.74 & 7.77(1H, dd, J=1.7, 8.6 Hz), 7.89 & 7.92(1H, dd, J=1.7, 8.6 Hz), 8.05 & 8.10(1H, d, J=1.7 Hz), 8.16 & 8.21(1H, d, J=1.7 Hz), 8.86 & 9.08(1H, d, J=8.6 Hz), 9.90 & 9.91(1H, s).

FAB-MS (m/e, as $(C_{32}H_{41}O_5N_2I-I)^+$):533

EXAMPLE 44

Synthesis of N-[1-(cyclooctylmethyl)piperidin-4-yl]-2,7-bis(methoxycarbonyl)xanthene-9-carboxamide Step 1. Synthesis of 9-t-butoxycarbonyl-7-methoxycarbonylxanthene-2-carboxylic acid 41 mg of sodium chlorite was added to 1.0 ml water-2.0 ml t-butanol solution having 140 mg of t-butyl 2-formyl-7-methoxycarbonylxanthene-9-carboxylate, 0.05 ml of 2-methyl-2-butene and 21 mg of sodium dihydrogen phosphate, followed by stirring for 2 hours at room temperature. The reaction solution was acidified with 1N hydrochloric acid, followed by extraction with ethyl acetate and drying over anhydrous magnesium sulfate. The solvent was distilled off under reduced pressure, and 52 mg of the title compound as a colorless solid was obtained.

Step 2. Synthesis of t-butyl 2,7-bis(methoxycarbonyl) xanthene-9-carboxylate

The title compound was synthesized in the same manner as in Step 2 of Example 38.

Step 3. Synthesis of 2,7-bis(methoxycarbonyl)xanthene-9-carboxylic acid

The title compound was synthesized in the same manner as in Step 3 of Example 38.

Step 4 Synthesis of N-[1-(cyclooctylmethyl)piperidin-4-yl]-2,7-bis(methoxycarbonyl)xanthene-9-carboxamide The title compound was synthesized in the same manner as in Example 20.

$^1$H-NMR(CDCl$_3$, δ ppm):1.09–1.88(19H, m), 1.88–2.12 (4H, m), 2.52–2.75(2H, m), 3.60–3.75(1H, m), 3.92(6H, s), 4.86(1H, s), 5.10–5.18(1H, m), 7.20(2H, d, J=8.6 Hz), 8.02(2H, dd, J=2.0, 8.6 Hz), 8.10(2H, d, J=2.0 Hz).

FAB-MS(m/e, as $(C_{32}H_{40}O_6N_2+H)^+$):549

EXAMPLE 45

Synthesis of 1-cyclooctylmethyl-1-methyl-4-[2,7-bis (methoxycarbonyl]xanthene-9-carboxamido) piperidinium iodide The title compound was synthesized in the same manner as in Example 11 by using N-[1-(cyclooctylmethyl) piperidin-4-yl]-2,7-bis(methoxycarbonyl)xanthene-9-carboxamide.

$^1$H-NMR(CDCl$_3$, δ ppm):1.40–2.55(19H, m), 3.15 & 3.47(3H, s), 3.38 & 3.77(2H, d, J=4.0 Hz), 3.52–4.52(5H, m), 3.86(6H, s), 5.46 & 5.75(1H, s), 7.02 & 7.09(2H, d, J=8.6 Hz), 7.84&7.89(2H, dd, J=2.0, 8.6 Hz), 8.09 & 8.15(2H, d, J=2.0 Hz), 8.82 & 9.05(1H, d, J=8.2 Hz).

FAB-MS(m/e, as $(C_{33}H_{43}O_6N_2I-I)^+$):563

EXAMPLE 46

Synthesis of 1-cyclooctylmethyl-1-methyl-4-(2-bromo-7-carbamoylxanthene-9-carboxamido) piperidinium iodide Step 1. Synthesis of t-butyl 2-bromo-7-carbamoylxanthene-9-carboxylate 2.0 ml of N,N-dimethylformamide solution having 290 mg of 7-bromo-9-t-butoxycarbonylxanthene-2-carboxylic acid, 75 mg of ammonium chloride, 200 mg of EDCI.HCl, 145 mg of 1-hydroxybenzotriazole and 0.20 ml of triethylamine, was stirred for 12 hours at room temperature. 10% aqueous citric acid solution was added to the reaction solution, followed by extraction with ethyl acetate. The organic layer was washed with saturated aqueous sodium bicarbonate and water, and dried over anhydrous magnesium sulfate. The solvent was distilled off under reduced pressure, and 289 mg of the title compound as a colorless solid was obtained.

Step 2. Synthesis of 2-bromo-7-carbamoylxanthene-9-carboxylic acid

The title compound was synthesized in the same manner as in Step 3 of Example 38.

Step 3. Synthesis of N-[1-(cyclooctylmethyl)piperidin-4-yl]-2-bromo-7-carbamoylxanthene-9-carboxamide The title compound was synthesized in the same manner as in Example 20.

Step 4. Synthesis of 1-cyclooctylmethyl-1-methyl-4-(2-bromo-7-carbamoylxanthene-9-carboxamido)piperidinium iodide The title compound was synthesized in the same manner as in Example 11 by using N-[1-(cyclooctylmethyl) piperidin-4-yl]-2-bromo-7-carbamoylxanthene-9-carboxamide.

$^1$H-NMR((CD$_3$)$_2$SO, δ ppm):1.10–2.20(19H, m), 3.03 (3H, s), 3.10–3.52(6H, m), 3.65–3.85(1H, m), 4.96(1H, s), 7.15(1H, d, J=8.7 Hz), 7.20(1H, d, J=8.6 Hz), 7.33(1H, br. s), 7.49(1H, dd, J=2.4, 8.7 Hz), 7.54 & 7.56(1H, d, J=2.4 Hz), 7.83(1H, dd, J=2.3, 8.6 Hz), 7.85 & 7.90(1H, d, J=2.3 Hz), 7.93(1H, br. s), 8.48 & 8.52(1H, d, J=7.6 Hz).

FAB-MS(m/e, as $(C_{30}H_{39}O_3N_3BrI-I)^+$):568, 570

EXAMPLE 47

Synthesis of N-[1-(cyclooctylmethyl)piperidin-4-yl]-2-hydroxymethyl-7-methoxycarbonylxanthene-9-carboxamide 12 mg of N-[1-(cyclooctylmethyl)piperidin-4-yl]-2-formyl-7-methoxycarbonylxanthene-9-carboxamide was dissolved in 1.0 ml of ethanol, 10 mg of sodium borohydride was added thereto, followed by stirring for 40 minutes at room temperature. Sodium sulfate decahydrate was added to the reaction solution, followed by drying over anhydrous sodium sulfate. The solvent was distilled off under reduced pressure, the obtained residue was purified by preparative thin layer chromatography (Kieselgel™60F$_{254}$, Art5744 produced by Merck Co.: chloroform/methanol=95/5), and 10 mg of the title compound as a colorless solid was obtained.

$^1$H-NMR(CDCl$_3$, δ ppm):1.05–1.80(19H, m), 1.85–2.05 (4H, m), 2.50–2.69(2H, m), 3.58–3.75(1H, m), 3.91(3H, s), 4.69(2H, s), 4.84(1H, s), 5.16(1H, d, J=8.2 Hz), 7.15(1H, d, J=8.6 Hz), 7.17(1H, d, J=8.6 Hz), 7.34(1H, dd, J=2.0, 8.6 Hz), 7.39(1H, d, J=2.0 Hz), 7.99(1H, dd, J=2.0, 8.6 Hz), 8.10(1H, d, J=2.0 Hz).

FAB-MS(m/e, as $(C_{31}H_{40}O_5N_2+H)^+$):521

EXAMPLE 48

Synthesis of 1-cyclooctylmethyl-1-methyl-4-(2-bromo-7-benzyloxycarbonylxanthene-9-carboxamido)piperidinium iodide Step 1. Synthesis of t-butyl 2-benzyloxycarbonyl-7-bromoxanthene-9-carboxylate 3.6 g of N,N'-diisopropyl-O-benzylisourea was added to THF solution having 2.06 g of 7-bromo-9-t-butoxycarbonylxanthene-2-carboxylic acid, followed by stirring for 14 hours. The solvent was distilled off under reduced pressure, the obtained residue was purified by silica gel column chromatography (developing solvent: hexane/ ethyl acetate=9/1), and 1.32 g of the title compound was obtained.

Step 2. Synthesis of 2-benzyloxycarbonyl-7-bromoxanthene-9-carboxylic acid

The title compound was synthesized in the same manner as in Step 3 of Example 38.

Step 3. Synthesis of N-[1-(cyclooctylmethyl)piperidin-4-yl]-2-benzyloxycarbonyl-7-bromoxanthene-9-carboxamide The title compound was synthesized in the same manner as in Example 20.

Step 4. Synthesis of 1-cyclooctylmethyl-1-methyl-4-(2-benzyloxycarbonyl-7-bromoxanthene-9-carboxamido) piperidinium iodide The title compound was synthesized in the same manner as in Example 11 by using N-[1-(cyclooctylmethyl) piperidin-4-yl]-2-benzyloxycarbonyl-7-bromoxanthene-9-carboxamide $^1$H-NMR(CDCl$_3$, δ ppm):1.38–2.50(19H, m), 3.36 & 3.07(3H, s), 3.22–4.45(7H, m), 5.29(1H, d, J=12.8 Hz), 5.33(1H, d, J=12.8 Hz), 5.73 & 5.42(1H, s), 6.89 & 6.94(1H, d, J=8.6 Hz), 7.02 & 7.06(1H, d, J=8.6 Hz), 7.22–7.48(6H, m), 7.60 & 7.69(1H, d, J=2.2 Hz), 7.89 & 7.92(1H, dd, J=1.9, 8.6 Hz), 8.10 & 8.14(1H, d, J=1.9 Hz), 8.81 & 9.01(1H, d, J=8.4 Hz).

FAB-MS (m/e, as $(C_{37}H_{44}O_4N_2BrI-I)^+$):659, 661

EXAMPLE 49

Synthesis of 1-cyclooctylmethyl-1-methyl-4-(2-methylcarbamoylxanthene-9-carboxamido) piperidinium iodide Step 1. Synthesis of N-[1-(cyclooctylmethyl)piperidin-4-yl]-2-carboxyxanthene-9-carboxamide 1.55 g of N-[1-(cyclooctylmethyl)piperidin-4-yl]-2-benzyloxycarbonyl-7-bromoxanthene-9-carboxamide was dissolved in 100 ml methanol-100 ml THF, 300 mg of 10% palladium—carbon catalyst was added thereto, followed by catalytic reduction for 8 hours at room temperature under hydrogen normal pressure. The catalyst was removed by filtration, the filtrate was distilled off under reduced pressure, and 1.10 g of the title compound as a colorless solid was obtained.

Step 2. Synthesis of N-[1-(cyclooctylmethyl)piperidin-4-yl]-2-methylcarbamoylxanthene-9-carboxamide 1.5 ml of N,N-dimethylformamide solution having 40 mg of N-[1-(cyclooctylmethyl)piperidin-4-yl]-2-carboxylxanthene-9-carboxamide, 10 mg of methylamine hydrochloride, 125 mg of EDCI.HCl, 20 mg of 1-hydroxybenzotriazole and 0.1 ml of triethylamine, was stirred for 12 hours at room temperature. Saturated aqueous sodium bicarbonate was added to the reaction solution, followed by extraction with ethyl acetate. The organic layer was washed with water, and dried over anhydrous sodium sulfate. The solvent was distilled off under reduced pressure, the obtained residue was purified by preparative thin layer chromatography (Kieselge™60F$_{254}$, Art5744 produced by Merck Co.: chloroform/methanol=95/5), and 14 mg of the title compound as a colorless solid was obtained.

Step 3. Synthesis of 1-cyclooctylmethyl-1-methyl-4-(2-methylcarbamoylxanthene-9-carboxamido)piperidinium iodide The title compound was synthesized in the same manner as in Example 11 by using N-[1-(cyclooctylmethyl) piperidin-4-yl]-2-methylcarbamoylxanthene-9-carboxamide.

$^1$H-NMR(CDCl$_3$, δ ppm):1.20–2.65(19H,m), 2.88–4.03 (13H, m), 4.10–4.30(1H, m), 5.13 & 5.31(1H, s), 7.01–8.58 (8H, m).

FAB-MS (m/e, as $(C_{31}H_{42}O_3N_3I-I)^{30}$):504

EXAMPLE 50

Synthesis of 1-cyclooctylmethyl-1-methyl-4-(2-dimethylcarbamoylxanthene-9-carboxamido) piperidinium iodide The title compound was synthesized in the same manner as in Example 49 by using THF solution having dimethylamine.

$^1$H-NMR(CDCl$_3$, δ ppm):1.05–2.43(19H, m), 2.97 & 3.21(3H, s), 3.19(6H, s), 3.35–4.28(7H, m), 5.27 & 5.59(1H, s), 7.05–7.68 (7H, m), 8.61 & 8.86(1H, d, J=8.2 Hz).

FAB-MS (m/e, as $(C_{32}H_{44}O_3N_3I-I)^+$):518

EXAMPLE 51

Synthesis of 1-cyclooctylmethyl-1-methyl-4-(2-ethoxycarbonylmethylcarbamoylxanthene-9-carboxamido)piperidinium iodide The title compound was synthesized in the same manner as in Example 49 by using glycine ethyl ester hydrochloride.

$^1$H-NMR(CDCl$_3$, δ ppm):1.10–2.40(22H, m), 2.92 & 3.03(3H, s), 2.85–4.40(11H, m), 5.09 & 5.31(1H, s), 7.00–8.65(9H, m).

FAB-MS (m/e, as $(C_{34}H_{46}O_5N_3I-I)^+$):576

EXAMPLE 52

Synthesis of 1-cyclooctylmethyl-1-methyl-4-(2-phenethylcarbamoylxanthene-9-carboxamido) piperidinium iodide The title compound was synthesized in the same manner as in Example 49 by using phenethylamine.

$^1$H-NMR(CDCl$_3$, δ ppm):1.18–2.60(19H, m), 2.93 & 3.23(3H, s), 3.02(2H, t, J=7.6 Hz), 2.90–4.30(10H, m), 5.18 & 5.35(1H, s), 6.91–7.40(10H, m), 7.80(1H, dd, J=2.2, 8.5 Hz), 8.44&8.56(1H, d, J=2.2 Hz), 8.49 & 8.67(1H, d, J=8.5 Hz).

FAB-MS (m/e, as $(C_{38}H_{48}O_3N_3I-I)^+$):594

EXAMPLE 53

Synthesis of N-[1-(cyclooctylmethyl)piperidin-4-yl]-2-benzylcarbamoylxanthene-9-carboxamide The title compound was synthesized in the same manner as in Example 49 by using benzylamine.

$^1$H-NMR(CDCl$_3$, δ ppm):1.09–2.20(23H, m), 2.55–2.75 (2H, m), 3.58–3.75(1H, m), 4.55–4.72(2H, m), 4.84(1H, s), 5.20–5.40(1H, m), 6.41–6.58(1H, m), 7.09–7.45(10H, m), 7.80(1H, d, J=8.4 Hz), 7.87(1H, s).

FAB-MS(m/e, as $(C_{36}H_{43}O_3N_3+H)^+$): 566

EXAMPLE 54

Synthesis of 1-cyclooctylmethyl-1-methyl-4-(2-benzylcarbamoylxanthene-9-carboxamido) piperidinium iodide The title compound was synthesized in the same manner as in Example 11 by using N-[1-(cyclooctylmethyl) piperidin-4-yl]-2-benzylcarbamoylxanthene-9-carboxamide.

$^1$H-NMR(CDCl$_3$, δ ppm):1.18–2.53(19H, m), 2.87 & 3.04(3H, s), 3.10–4.29(8H, m), 4.47–4.82(2H, m), 5.17&5.35(1H, s), 7.00–8.68(13H, m).

FAB-MS (m/e, as $(C_{37}H_{46}O_3N_3I-I)^+$):580

EXAMPLE 55

Synthesis of N-[1-(1-cyclooctenylmethyl)piperidin-4-yl]-xanthene-9-carboxamide

The title compound was synthesized in the same manner as in Step 3 of Example 1 by using 1-cyclooctenecarbaldehyde.

$^1$H-NMR(CDCl$_3$, δ ppm):1.03–2.85(22H, m), 3.58–3.75 (1H, m), 4.84(1H, s), 5.01–5.18(1H, m), 6.35–6.48(1H, m), 7.10(2H, t, J=7.6 Hz), 7.13(2H, d, J=7.6 Hz), 7.30(2H, t, J=7.6 Hz), 7.38(2H, d, J=7.6 Hz).

FAB-MS (m/e, as $(C_{28}H_{34}O_2N_2+H)^+$):431

EXAMPLE 56

Synthesis of 1-(1-cyclooctenylmethyl)-1-methyl-4-(xanthene-9-carboxamido)piperidinium iodide The title compound was synthesized in the same manner as in Example 11 by using N-[1-(1 -cyclooctenylmethyl) piperidin-4-yl]-xanthene-9-carboxamide.

$^1$H-NMR(CDCl$_3$, δ ppm):1.30–2.49(16H, m), 2.90 & 3.13(3H, s), 3.31–3.68(4H, m), 3.82 & 4.18(2H, s), 3.92–4.30(1H, m), 5.14 & 5.42(1H, s), 5.99 & 6.12(1H, t, J=8.3 Hz), 7.02(2H, t, J=8.3 Hz), 7.04(2H, d, J=8.3 Hz), 7.21(2H, t, J=8.3 Hz), 7.42 & 7.48(2H, d, J=8.3 Hz), 8.26 & 8.52(1ll, d, J=8.3 Hz).

FAB-MS (m/e, as $(C_{29}H_{37}O_2N_2I-I)^+$):445

EXAMPLE 57

Synthesis of 1-cyclodecylmethyl-1-methyl-4-(xanthene-9-carboxamido)piperidinium iodide The title compound was synthesized in the same manner as in Example 11 by using N-[1-(1-cyclodecylmethyl) piperidin-4-yl]-xanthene-9-carboxamide.

$^1$H-NMR(CDCl$_3$, δ ppm):1.10–2.48(23H, m), 2.96 & 3.25(3H, s), 3.13 & 3.55(2H, d, J=4.0 Hz), 3.35–4.29(5H, m), 5.18 & 5.41(1H, s), 7.02(2H, t, J=8.0 Hz), 7.06(2H, d, J=8.0 Hz), 7.21(2H, t, J=8.0 Hz), 7.46 & 7.50(2H, d, J=8.0 Hz), 8.47 & 8.75(1H, d, J=8.6 Hz).

FAB-MS (m/e, as (C$_{31}$H$_{43}$O$_2$N$_2$I–I)$^+$):475

EXAMPLE 58

Synthesis of 1-(1-cyclooctenylmethyl)-1-methyl-4-(2,7-dichloroxanthene-9-carboxamido)piperidinium iodide The title compound was synthesized in the same manner as in Example 11 by using N-[1-(1-cyclooctenylmethyl)piperidin-4-yl]-2,7-dichloroxanthene-9-carboxamide.

$^1$H-NMR(CDCl$_3$, δ ppm):1.35–2.52(16H,m),3.00 & 3.34 (3H, s), 3.28–4.60(5H, m), 3.93 & 4.37(2H, s), 5.30 & 5.66(1H, s), 6.08 & 6.26(1H, t, J=8.3 Hz), 6.98 & 6.99(2H, d, J=8.6 Hz), 7.17(2H, d d, J=2.3, 8.6 Hz), 7.41 & 7.51(2H, d, J=2.3 Hz), 8.73 & 8.99(1H, d, J=8.5 Hz).

FAB-MS (m/e, as (C$_{29}$H$_{35}$O$_2$N$_2$C$_2$I–I)$^+$):513

EXAMPLE 59

Synthesis of cis*-1-(1-cyclooctenylmethyl)-1-ethyl-4-(2,7-dichloroxanthene-9-carboxamido)piperidinium iodide and trans*-1-(1-cyclooctenylmethyl)-1-ethyl-4-(2,7-dichloroxanthene-9-carboxamido)piperidinium iodide The title compound was synthesized in the same manner as in Example 26 by using N-[1-(1-cyclooctenylmethyl)piperidin-4-yl]-2,7-dichloroxanthene-9-carboxamide.

cis*-1-(1-cyclooctenylmethyl)-1-ethyl-4-(2,7-dichloroxanthene-9-carboxamido)piperidinium iodide $^1$H-NMR(CDCl$_3$, δ ppm):1.40(3H, t, J=7.3 Hz), 1.25–1.67(8H, m), 1.96–2.60(8H, m), 3.55–3.86(6H, m), 3.82(2H, s), 4.15–4.30(1H, m), 5.28(1H, s), 6.07(1H, t, J=8.2 Hz), 6.96(2H, d, J=8.7 Hz), 7.16(2H, dd, J=2.4, 8.7 Hz), 7.39(2H, d, J=2.4 Hz), 8.80(1H, d, J=7.8 Hz).

FAB-MS (m/e, as (C$_{30}$H$_{37}$O$_2$N$_2$Cl$_2$I–I)$^+$):527 trans*-1-(1-cyclooctenylmethyl)-1-ethyl-4-(2,7-dichloroxanthene-9-carboxamido)piperidinium iodide $^1$H-NMR(CDCl$_3$, δ ppm):1.35(3H, t, J=7.1 Hz), 1.38–1.74(8H, m), 1.98–2.45(8H, m), 3.22–3.40(4H, m), 4.24(2H, s), 4.38–4.40(1H, m), 4.41–4.60(2H, m), 5.69(1H, s), 6.26(1H, t, J=8.2 Hz), 7.00(2H, d, J=8.7 Hz), 7.17(2H, dd, J=2.5, 8.7 Hz), 7.51(2H, d, J=2.5 Hz), 9.08(1H, d, J=8.6 Hz).

FAB-MS(m/e, as (C$_{30}$H$_{37}$O$_2$N$_2$Cl$_2$I–I)$^+$):527

EXAMPLE 60

Synthesis of cis*-1-(1-cyclooctenylmethyl)-1-ethyl-4-(xanthene-9-carboxamido)piperidinium iodide and trans*-1-(1-cyclooctenylmethyl)-1-ethyl-4-(xanthene-9-carboxamido)piperidinium iodide The title compounds were synthesized in the same manner as in Example 26 by using N-[1-(1-cyclooctenylmethyl)piperidin-4-yl]-xanthene-9-carboxamide.

cis*-1-(1-cyclooctenylmethyl)-1-ethyl-4-(xanthene-9-carboxamido)piperidinium iodide $^1$H-NMR(CDCl$_3$, δ ppm):1.23(3H, t, J=7.3 Hz), 1.35–2.50(16H, m), 3.23–3.68(6H, m), 3.70(2H, s), 4.03–4.20(1H, m), 5.11(1H, s), 5.96(1H, t, J=8.2 Hz), 7.01 (2H, t, J=7.7 Hz), 7.03(2H, d, J=7.7 Hz), 7.20(2H, t, J=7.7 Hz), 7.41(2H, d, J=7.7 Hz), 8.34(1H, d, J=7.8 Hz).

FAB-MS (m/e, as (C$_{30}$H$_{39}$O$_2$N$_2$I–I)$^+$):459 trans*-1-(1-cyclooctenylmethyl)-1-ethyl-4-(xanthene-9-carboxamido)piperidinium iodide $^1$H-NMR(CDCl$_3$, δ ppm):1.24(3H, t, J=7.1 Hz), 1.35–2.41(16H, m), 3.15–3.35(4H, m), 3.95–4.15(2H, m), 4.08(2H, s), 4.15–4.32(1H, m), 5.44(1H, s), 6.15(1H, t, J=8.2 Hz), 7.01(2H, t, J=7.6 Hz), 7.05(2H, d, J=7.6 Hz), 7.20(2H, t, J=7.6 Hz), 7.49(2H, d, J=7.6 Hz), 8.75(1H, d, J=8.6 Hz).

FAB-MS(m/e, as (C$_{30}$H$_{39}$O$_2$N$_2$I–I)$^+$):459

EXAMPLE 61

Synthesis of N-[1-(1-cyclononenylmethyl)piperidin-4-yl]-xanthene-9-carboxamide

Step 1. Synthesis of cyclononanone p-toluenesulfonylhydrazone 0.5 ml of hydrochloric acid was added to 20 ml of methanol suspension having 2.29 g of cyclononanone and 3.0 g of p-toluenesulfonylhydrazide, followed by stirring for 16 hours at room temperature. The precipitated solid was obtained by filtration, and 3.0 g of the title compound as a colorless solid was obtained.

Step 2. Synthesis of 1-cyclononene-1-carbaldehyde 37 ml of 1.6 M of n-butyllithium in hexane solution was added to 45 ml of N,N,N',N'-tetramethylethylenediamine suspension having 4.5 g of cyclononanone p-toluenesulfonylhydrazone at a temperature of –78° C., followed by stirring for 30 minutes at room temperature. 5.7 ml of N,N-dimethylformamide was added to the reaction solution, followed by stirring for 1 hour at room temperature. Water was added to the reaction solution, followed by extraction with ethyl acetate. The organic layer was washed with 2N aqueous hydrochloric acid solution and saturated aqueous sodium chloride, and dried over anhydrous magnesium sulfate. The solvent was distilled off under reduced pressure, the obtained residue was purified by silica gel column chromatography (developing solvent: hexane/ethyl acetate=19/1), and 1.43 g of the title compound as a yellow oil was obtained.

Step 3. Synthesis of N-[1-(1 -cyclononenylmethyl)piperidin-4-yl]-xanthene-9-carboxamide The title compound was synthesized in the same manner as in Step 3 of Example 1 by using 1-cyclononenecarbaldehyde.

$^1$H-NMR(CDCl$_3$, δ ppm):1.00–2.68(22H, m), 2.74(2H, br. s), 3.59–3.75(1H, m), 4.84(1H, s), 5.11(1H, d, J=7.8 Hz), 5.36(1H, t, J=8.4 Hz), 7.10(2H, t,=7.6 Hz), 7.13(2H, d, J=7.6 Hz), 7.30(2H, t, J=7.6 Hz), 7.38(2H, d, J=7.6 Hz).

FAB-MS(m/e, as (C$_{29}$H$_{36}$O$_2$N$_2$+H)$^+$):445

EXAMPLE 62

Synthesis of cis*-1-(1-cyclooctenylmethyl)-1-ethyl-4-(2,7-dichloroxanthene-9-carboxamido)piperidinium bromide and trans*-1-(1-cyclooctenylmethyl)-1-ethyl-4-(2,7-dichloroxanthene-9-carboxamido)piperidinium bromide The title compounds were synthesized in the same manner as in Example 26 by using ethyl bromide.

cis*-1-(1-cyclooctenylmethyl)-1-ethyl-4-(2,7-dichloroxanthene-9-carboxamido)piperidinium bromide $^1$H-NMR(CDCl$_3$, δ ppm):1.42(3H, t, J=7.2 Hz), 1.20–1.75(8H, m), 1.97–2.45(8H, m), 3.45–3.95(6H, m), 3.83(2H, s), 4.10–4.25(1H, m), 5.33(1H, s), 6.05(1H, t, J=8.2 Hz), 6.97(2H, d, J=8.6 Hz), 7.15(2H, dd, J=2.4, 8.6 Hz), 7.43(2H, d, J=2.4 Hz), 9.47(1H, d, J=7.3 Hz).

FAB-MS(m/e, as (C$_{30}$H$_{37}$O$_2$N$_2$Cl$_2$Br–Br)$^+$):527 trans*-1-(1-cyclooctenylmethyl)-1-ethyl-4-(2,7-dichloroxanthene-9-carboxamido)piperidinium bromide $^1$H-NMR(CDCl$_3$, δ ppm):1.34(3H, t, J=7.1 Hz), 1.29–2.50(16H, m), 3.20–4.75(7H, m), 4.23(2H, s), 5.64(1H, s), 6.26(1H, t, J=8.2 Hz), 6.99(2H, d, J=8.7 Hz), 7.16(2H, dd, J=2.4, 8.7 Hz), 7.54(2H, d, J=2.4 Hz), 9.75(1H, d, J=9.2 Hz).

FAB-MS (m/e, as (C$_{30}$H$_{37}$O$_2$N$_2$Cl$_2$Br–Br)$^+$):527

EXAMPLE 63

Synthesis of cis*-1-(1-cyclononenylmethyl)-1-ethyl-4-(xanthene-9-carboxamido)piperidinium iodide and trans*-1-(1-cyclononenylmethyl)-1-ethyl-4-(xanthene-9-carboxamido)piperidinium iodide The title compounds were synthesized in the same manner as in Example 26 by using N-[1-(1-cyclononenylmethyl)piperidin-4-yl]-xanthene-9-carboxamide.

cis*-1-(1-cyclononenylmethyl)-1-ethyl-4-(xanthene-9-carboxamido)piperidinium iodide $^1$H-NMR(CDCl$_3$, δ ppm):1.28(3H, t, J=7.1 Hz), 1.32–1.66(10H, m),1.82–2.56(8H, m), 3.37–3.72(6H, m), 3.70(2H, s), 4.05–4.21(1H, m), 5.12(1H, s), 5.89(1H, t, J=8.7 Hz), 7.03(2H, t, J=7.6 Hz), 7.04(2H, d, J=7.6 Hz), 7.21(2H, t, J=7.6 Hz), 7.43(2H, d, J=7.6 Hz), 8.24(1H, d, J=8.4 Hz).

FAB-MS (m/e, as (C$_{31}$H$_{41}$O$_2$N$_2$I–I)$^+$):473 trans*-1-(1-cyclononenylmethyl)-1-ethyl-4-(xanthene-9-carboxamido)piperidinium iodide $^1$H-NMR(CDCl$_3$, δ ppm):1.27(3H, t, J=6.9 Hz), 1.32–1.70(10H, m), 1.88–2.39(8H, m), 3.15–3.35(4H, m), 4.11(2H, s), 4.06–4.32(3H, m), 5.48(1H, s), 6.11(1H, t, J=8.7 Hz), 7.02(2H, t, J=7.6 Hz), 7.06(2H, d, J=7.6 Hz), 7.21(2H, t, J=7.6 Hz), 7.51(2H, d, J=7.6 Hz), 8.73(I1L, d, J=8.6 Hz).

FAB-MS (m/e, as (C$_{31}$H$_{41}$O$_2$N$_2$I–I)$^+$):473

EXAMPLE 64

Synthesis of 1-(1-cyclononenylmethyl)-1-methyl-4-(xanthene-9-carboxamido)piperidinium iodide The title compound was synthesized in the same manner as in Example 11 by using N-[1-(1-cyclononenylmethyl)piperidin-4-yl]-xanthene-9-carboxamide.

$^1$H-NMR(CDCl$_3$, δ ppm):0.80–2.50(18H, m), 2.92 & 3.18(3H, s), 3.28–4.32(7H, m), 5.16 & 5.47(1H, s), 5.91 & 6.08(1H, t, J=8.6 Hz), 6.94–7.34(6H, m), 7.44 & 7.51(2H, d, J=7.7 Hz), 8.18 & 8.55(1H, d, J=8.5 Hz).

FAB-MS (m/e, as (C$_{30}$H$_{39}$O$_2$N$_2$I–I)$^+$):459

EXAMPLE 65

Synthesis of N-[1-(cyclooctylmethyl)piperidin-4-yl]-2-(3-pyridylmethyl)carbamoylxanthene-9-carboxamide The title compound was synthesized in the same manner as in Example 49.

$^1$H-NMR(CDCl$_3$, δ ppm):1.09–2.25(23H, m), 2.60–2.80 (2H, m), 3.58–3.75(1H, m), 4.66(2H, d, J=5.9 Hz), 4.85(1H, s), 5.33–5.51(1H, m), 6.72–6.84(1H, m), 7.10–7.40(6H, m), 7.73(1H, d, J=7.9 Hz), 7.82(1H, dd, J=2.0, 8.6 Hz), 7.93(1H, d, J=2.0 Hz), 8.53(1H, d, J=4.8 Hz), 8.64(1H, s)

FAB-MS (m/e, as (C$_{35}$H$_{42}$O$_3$N$_4$+H)$^+$):567

EXAMPLE 66

Synthesis of 1-cyclooctylmethyl-1-methyl-4-(2-(3-methylpyridiniummethyl)carbamoylxanthene-9-carboxamido)piperidinium diiodide The title compound was synthesized in the same manner as in Example 49.

$^1$H-NMR(CD$_3$OD, δ ppm):1.40–2.25(19H, m), 3.10 & 3.15(3H, s), 3.05–4.02(7H, m), 4.42(3H, s), 4.58(2H, s), 5.05 & 5.13(1H, s), 7.08–7.42(5H, m), 7.82–8.12(3H, m), 8.58(1H, d, J=8.2 Hz), 8.81(1H, d, J=5.9 Hz), 8.97(1H, s).

FAB-MS (m/e, as (C$_{37}$H$_{48}$O$_3$N$_4$I$_{2-I}$)$^+$):723

EXAMPLE 67

Synthesis of N-[1-(cyclooctylmethyl)piperidin-4-yl1-2-(4-pyridylmethyl) carbamoylxanthene-9-carboxamide The title compound was synthesized in the same manner as in Example 49.

$^1$H-NMR(CDC$_3$, δ ppm):1.10–2.25(231H, m), 2.60–2.82 (2H, m), 3.58–3.75(1H, m), 4.57–4.73(2H, m), 4.86(1H, s), 5.31–5.53(1H, m), 6.75–6.90(1H, m), 7.10–7.40(7, m), 7.83 (1H , dd, J=2.2, 8.5Hz), 7.94(1H, d, J=2.2 Hz), 8.57(2H, d, J=6.1 Hz).

FAB-MS (m/e, as (C$_{35}$H$_{42}$O$_3$N$_4$+H)$^+$)$^+$):567

EXAMPLE 68

Synthesis of 1-cyclooctylmethyl-1-methyl-4-[2-( 4-methylpyridiniummethyl)carbamoylxanthene-9-carboxamido]peridinium diiodide The title compound was synthesized in the same manner as in Example 49.

$^1$H-NMR(CD$_3$OD, δ ppm): 1.45–2.24(19H, m), 3.10 & 3.14(3H, s), 3.15–4.02(7H, m), 4.37(3H, s), 4.58(21H, s), 5.05 & 5.13(1H, s), 7.09–7.42(5H, m), 7.86–8.10(4H, m), 8.79–8.85(21H, m).

FAB-MS (m/e, as (C$_{37}$H$_{48}$O$_3$N$_4$I$_2$–I)$^+$):723

EXAMPLE 69

Synthesis of 1-cyclooctylmethyl-1-methyl-4-(2-benzyloxycarbonylxanthene-9-carboxamido) piperidinium iodide The title compound was synthesized in the same manner as in Example 49.

$^1$H-NMR(CDCl$_3$, δ ppm):1.20–2.50(19H, m), 3.02 & 3.31(3H, s), 3.15–4.33(7H, m), 5.32(2H, s), 5.32 & 5.61(1H, s), 6.99–7.67(10H, m), 7.91 & 7.94(1H, dd, J=2.0, 8.6 Hz), 8.06 & 8.09(1H, d, J=2.0 Hz), 8.59 & 8.81(1H, d, J=8.9 Hz).

FAB-MS(m/e, as $(C_{37}H_{45}O_4N_2I-I)^+$):581

EXAMPLE 70

Synthesis of N-[1-(1-cyclononenylmethyl)piperidin-4-yl]-2-methoxycarbonylxanthene-9-carboxamide The title compound was synthesized in the same manner as in Example 20.

$^1$H-NMR(CDCl$_3$, δ ppm): 1.10–2.15(20H, m), 2.48–2.53 (2H, m), 2.71(2H, s), 3.59–3.75(1H, m), 3.91(3H, s), 4.85 (1H, s), 5.11(1H, d, J=8.1 Hz), 5.35(1H, t, J=8.5 Hz), 7.10–7.19(2H, m), 7.13(1H, d, J=8.5 Hz), 7.29–7.40(2H, m), 7.99(1H, dd, J=2.0, 8.5 Hz), 8.14(1H, d, J=2.0 Hz).

FAB-MS (m/e, as $(C_{31}H_{38}O_4N_2+H)^+$):503

EXAMPLE 71

Synthesis of N-[1-(1-cyclononenylmethyl)piperidin-4-yl]-2-benzylcarbamoylxanthene-9-carboxamide The title compound was synthesized in the same manner as in Example 49.

$^1$H-NMR(CDCl$_3$, δ ppm): 1.10–2.20(20H, m), 2.50–2.56 (2H, m), 2.73(2H, s), 3.55–3.74(1H, m), 4.61(1H, dd, J=5.6, 14.4 Hz), 4.67(1h, dd, J=5.6, 14.4 Hz), 4.83(1H, s), 5.16 (1H, d, J=7.8 Hz), 5.36(1H, t, J=8.5 Hz), 6.48(1H, t, J=5.6 Hz), 7.10–7.21(3H, m), 7.24–7.41(7H, m), 7.81(1H, dd, J=2.1, 8.6 Hz), 7.86(1H, d, J=2.1 Hz).

FAB-MS (m/e, as $(C_{37}H_{43}O_3N_3+H)^+$):578

EXAMPLE 72

Synthesis of N-[1-(1-cyclononenylmethyl)piperidin-4-yl]-2-(3-pyridylmethyl)carbamoylxanthene-9-carboxamide The title compound was synthesized in the same manner as in Example 49.

$^1$H-NMR(CDCl$_3$, δ ppm):1.19–2.22(20H, m), 2.58–2.74 (2H, m), 2.77(2H, s), 3.55–3.74(1H, m), 4.58(1H, dd, J=5.8, 14.7 Hz), 4.63(1H, dd, J=5.8, 14.7 Hz), 4.82(1H, s), 5.38 (1H, t, J=8.4 Hz), 5.60–5.85(1H, m), 7.05–7.41(7H, m), 7.70(1H, ddd, J=1.6, 2.2, 7.9 Hz), 7.76(1H, dd, J=2.1, 8.5 Hz), 7.90(1H, d, J=2.1 Hz), 8.50(1H, dd, J=1.6, 4.8 Hz), 8.59(1H, d, J=2.2 Hz).

FAB-MS (m/e, as $(C_{36}H_{42}O_3N_4+H)^+$): 579

EXAMPLE 73

Synthesis of N-[1-(1-cyclononenylmethyl)piperidin-4-yl]-2-(2-pyridylmethyl)carbamoylxanthene-9-carboxamide The title compound was synthesized in the same manner as in Example 49.

$^1$H-NMR(CDCl$_3$, δ ppm):1.16–2.21(20H, m), 2.50–2.69 (2H, m), 2.75(2H, s), 3.58–3.75(1H, m), 4.68–4.82(2H, m), 4.88(1H, s), 5.23(1H, d, J=8.4 Hz), 5.37(1H, t, J=8.4 Hz), 7.09–7.75(9H, m), 7.87(1H, dd, J=2.0, 8.6 Hz), 7.95(1H, d, J=2.0 Hz), 8.58(1H, dd, J=0.9, 5.0 Hz).

FAB-MS (m/e, as $(C_{36}H_{42}O_3N_4+H)^+$): 579

INDUSTRIAL APPLICABILITY

The compounds of the present invention have antagonism against chemokine receptors, and thus useful as treating agents for various diseases relating to chemokines, such as acute inflammatory diseases, chronic inflammatory diseases, acquired immune deficiency syndrome, cancer, ischemic reflow disorder and/or arteriosclerosis.

What is claimed is:

1. A compound of the formula:

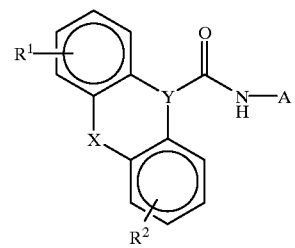

(I)

wherein each of $R^1$ and $R^2$, which are the same or different, is hydrogen, halogen, lower alkyl, lower alkenyl, lower alkynyl, hydroxy lower alkyl, lower alkoxy, lower alkoxycarbonyl, aralkyloxycarbonyl, formyl, carbamoyl, lower alkylaminocarbonyl, di-lower alkylaminocarbonyl, lower alkoxycarbonyl (lower)alkylaminocarbonyl aralkyloxy-carbonyl (lower)alkylaminocarbonyl, aralkylaminocarbonyl, diaralkylaminocarbonyl or heteroaryl(lower) alkylaminocarbonyl, wherein the heteroaryl group of the heteroaryl(lower) alkylaminocarbonyl contains one to three heteroatoms selected from the group consisting of oxygen, nitrogen and sulfur, and when it contains at least one nitrogen, it optionally forms a quaternary salt with a lower alkyl group or a lower alkenyl group; X is oxygen, sulfur or CH; Y is CH; A is a group of the formula:

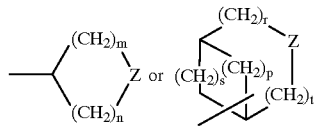

wherein each of m and n is from 1 to 3, m+n is from 3 to 5, p is from 1 to 3, each of r, s and t which are the same or different, is from 0 to 3, r+s+t is from 2 to 3, and Z is a group of the formula:

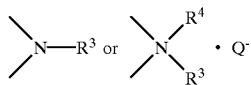

wherein $R^3$ is $C_{5-15}$ saturated or unsaturated aliphatic hydrocarbon; $R^4$ is lower alkyl or lower alkenyl, and Q– is an anion, or a pharmaceutically acceptable salt thereof, or a hydrate thereof.

2. The compound of claim 1, wherein each of m and n is 2.

3. The compound of claim 1, wherein $R^3$ is cyclooctylmethyl, cyclononylmethyl, 1-decylmethyl, 2-decylmethyl, (1-cyclooctenyl)methyl or (1-cyclononenyl)methyl.

4. The compound of claim 1, wherein $R^4$ is methyl, ethyl, propyl or allyl.

5. The compound of claim 1, wherein X is oxygen or sulfur.

6. The compound of claim 1, which is N-(1-(cyclooctylmethyl)piperidin-4-yl]xanthene-9-carboxamide, N-[1-(cyclooctylethyl)piperidin-4-yl]xanthene-9-carboxamide, N-[1-(cyclooctylpropyl)piperidin-4-yl]xanthene-9-carboxamide, N-[1(cyclononylmethyl)piperidin-4-yl]xanthene-9-carboxamide, N-[1-(cyclohexylmethyl)piperidin-4-yl]xanthene-9-carboxamide, N-[(2-decylmethylpiperidin-4-yl)]xanthene-9-carboxamide, N-(1-hexylpiperidin-4-yl)xanthene-9-carboxamide, N-[9-(cyclooctylmethyl)-9-azabicyclo[3.3.1]nonan-3-yl]xanthene-9-carboxamide, 1-cyclooctylmethyl-1-methyl-4-(xanthene-9-carboxamido)piperidinium, 1-cyclooczylmethyl-1-ethyl-4-(xanthene-9-carboxamido)piperidinium iodide, 1-cyclooctylmethyl-1-propyl-4-(xanthene-9-carboxamido)piperidinium iodide, 1-allyl-1-cyclooctylmethyl-4-(xanthene-9-carboxamido)piperidinium bromide, 1-cyclononylmethyl-1-methyl-4-(xanthene-9-carboxamido)piperidinium iodide, 1(1-decylmethyl)-1-methyl-4-(xanthene-9 -carboxamido)piperidinium iodide, 1-(2-decylmethyl)-1-methyl-4-(xanthene-9-carboxamido)piperidinium iodide, 1-hexyl-1-methyl-4-(xanthene-9-carboxamido)piperidinium iodide, N-[1-(1-cyclohexylethyl)piperidin-4-yl]-xanthene-9-carboxamide iodide, N-[1-(cyclooctylmethyl)piperidin-4yl]-2,7-dibromoxanthene-9-carboxamide iodide, 1-cyclooctylmethyl-1-methyl-4-(2,7-dibromoxanthene-9-carboxamido)piperidinium iodide, 1-cyclooctylmethyl-1-butyl-4-(xanthene-9-carboxamido)piperidinium iodide, 1-(1-adamantylmethyl)-1-methyl-4-(xanthene-9-carboxamido)piperidinium iodide, 1-cyclooctylethyl-1-methyl-4-(xanthene-9-carboxamido)piperidinium iodide, cis-1-cyclooctylmethyl-1-ethyl-4-(2,7-dibromoxanthene-9-carboxamido)piperidinium iodide, trans-1-cyclooctylmethyl-1-ethyl-4-(2,7-dibromoxanthene-9-carboxamido)piperidinium iodide, 1-cyclooctylmethyl-1-propyl-4-(2,7-dibromoxanthene-9-carboxamido)piperidinium iodide, 1-cyclooctylmethyl-1-methyl-4-(2,7-divinylxanthene-9-carboxamido)piperidinium iodide, 1-cyclooctylmethyl-1-methyl-4-(2-bromoxanthene-9-carboxamido)piperidinium iodide, 1-cyclooctylmethyl-1-methyl-4-(2,7-diethylxanthene-9-carboxamido)piperidinium iodide, 1-cyclooctylmethyl-1-methyl-4-(2,7-dichloroxanthene-9-carboxamido)piperidinium iodide, 1-cyclooctylmethyl-1-methyl-4-(thioxanthene-9-carboxamido)piperidinium iodide, 1-cyclooctylmethyl-1-methyl-4-(2,7-dimethylxanthene-9-carboxamido)piperidinium iodide, 1-cyclooctylmethyl-1-methyl-4-(3,6-dimethylxanthene-9-carboxamido)piperidinium iodide, 1-cyclooctylmethyl-1-methyl-4-(3-methylxanthene-9-carboxamido)piperidinium iodide, 1-cyclooctylmethyl-1-methyl-4-(3-methoxyxanthene-9-carboxamido)piperidinium iodide, 1-cyclooctylmethyl-1-methyl-4-(3,6-dimethoxyxanthene-9-carboxamido)piperidinium iodide, N-[1-(cyclooctylmethyl)piperidin-4-yl]-2-bromo-7-methoxycarbonylxanthene-9-carboxamide, 1-cyclooctylmethyl-1-methyl-4-(2-bromo-7 -methoxycarbonylxanthene-9-carboxamido)piperidinium iodide, N-[1-(cyclooctylmethyl)piperidin-4-yl]-2-methoxycarbonylxanthene-9-carboxamide, 1-cyclooctylmethyl-1-methyl-4-(2-methoxycarbonylxanthene-9-carboxamido)piperidinium iodide, N-[1-(cyclooctylmethyl)piperidin-4-yl]-2,7-bis(methoxycarbonyl)xanthene-9-carboxamide, 1-cyclooctylmethyl-1-methyl-4-[2,7-bis(methoxycarbonyl)xanthene-9-carboxamido]piperidinium iodide, N-[1-(cyclooctylmethyl)piperidin-4-yl]-2-formyl-7-methoxycarbonylxanthene-9-carboxamide, 1-cyclooctylmethyl-1-methyl-4-(2-formyl-7-methoxycarbonylxanthene-9-carboxamido)piperidinium iodide, 1-cyclooctylmethyl-1-methyl-4-(2-bromo-7-carbamoylxanthene-9-carboxamido )piperidinium iodide, N-[1-(cyclooctymethyl)piperidium-4-yl]-2-hydroxymethyl-7-methoxycarbonlxanthene-9-carboxamide, 1-cyclooctylmethyl-1-methyl-4-(2-bromo-7-benzyloxycarbonylxanthene-9-carboxamido)piperidinium iodide, 1-cyclooctylmethyl-1-methyl-4-(2-methylcarbamoylxanthene-9-carboxamido)piperidinium iodide, 1-cyclooctylmethyl-1-methyl-4-(2-dimethylcarbamoylxanthene-9-carboxamido)piperidinium iodide, 1-cyclooctylmethyl-1-methyl-4-(2-ethoxycarbonylmethylcarbamoylxanthene-9-carboxamido)piperidinium iodide, 1-cyclooctylmethyl-1-methyl-4-(2-phenethylcarbamoylxanthene-9-carboxamido)piperidinium iodide, N-[1-cyclooctylmethyl)piperidin-4-yl]-2-benzylcarbamoylxanthene-9-carboxamide, 1-cyclooctylmethyl-1-methyl-4-(2-benzylcarbamoylxanthene-9-carboxamido)piperidinium iodide, N-[1-(1-cyclooctenylmethyl)piperidin-4-yl]-xanthene-9-carboxamide, 1-(1-cyclooctenylmethyl)-1-methyl-4-(xanthene-9-carboxamido)piperidinium iodide, 1-cyclodecanylmethyl-1-methyl-4-(xanthene-9-carboxamido)piperidinium iodide, 1-(1-cyclooctenylmethyl)-1-methyl-4-(2,7-dichloroxanthene-9-carboxamido)piperidinium iodide, cis-1-(1-cyclooctenylmethyl)-1-ethyl-4-(2,7-dichloroxanthene-9-carboxamido)piperidinium iodide, trans-1-(1-cyclooctenylmethyl)-1-ethyl-4-(2,7-dichloroxanthene-9-carboxamido)piperidinium iodide, cis-1-(1-cyclooctenylmethyl)-1-ethyl-4-(xanthene-9-carboxamido)piperidinium iodide, trans-1-(1-cyclooctenylmethyl)-1-ethyl-4-(xanthene-9-carboxamido)piperidinium iodide, cis-1-(1-cyclononenylmethyl)-1-ethyl-4-(xanthene-9-carboxamido)piperidinium iodide, trans-1-(1-cyclononenylmethyl)-1-ethyl-4-(xanthene-9-carboxamido)piperidinium iodide, cis-1-(1-cyclooctenylmethyl)-1-ethyl-4-(2,7-dichloroxanthene-9-carboxamido)piperidinium bromide and trans-1-(1-cyclooctenylmethyl)-1-ethyl-4-(2,7-dichloroxanthene-9-carboxamido)piperidinium bromide, N-[1-(1-cyclononenylmethyl)piperidin-4-yl]-xanthene-9-carboxamide, 1-(1-cyclononenylmethyl)-1-methyl-4-(xanthene-9-carboxamido)piperidinium iodide, N-[1 (cyclooctylmethyl)piperidin-4-yl]-2-(3-pyridylmethyl)carbamoylxanthene-9-carboxamide, 1-cyclooctylmethyl-1-methyl-4-(2-(3-methylpyridiniummethyl)carbamoylxanthene-9-carboxamido)piperidinium iodide, N-[1-(cyclooctylmethyl)piperidin-4-yl]-2-(4-pyridylmethyl)carbamoylxanthene-9-carboxamide, 1-cyclooctylmethyl-1-methyl-4-(2-(4-methylpyridiniummethyl)carbamoylxanthene-9-carboxamido)piperidinium diiodide or 1-cyclooctylmethyl-1-methyl-4-(2-benzyloxycarbonylxanthene-9-carboxamido)piperidinium iodide, a pharmaceutically acceptable salt thereof, or a hydrate thereof.

7. A method for producing a compound of the formula (I) as defined in claim 1, which comprises condensing a compound of the formula:

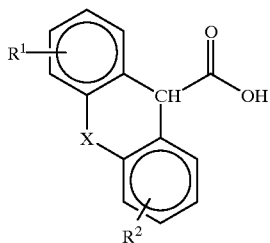

(II)

wherein $R^1$, $R^2$ and X are as defined in claim 1, with a compound of the formula:

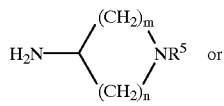

(III)

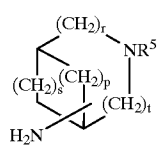

(IV)

wherein $R^5$ is $R^3$ as defined in claim 1 or is a protecting group, and m, n, p, r, s and t are as defined in claim 1, to form a compound of the formula:

(Va)

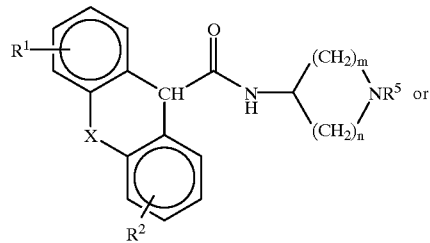

(Vb)

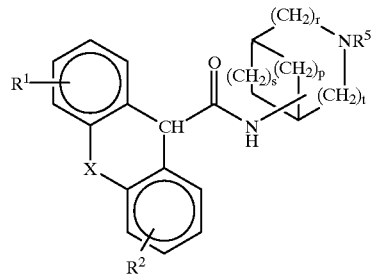

wherein $R^1$, $R^2$, $R^5$, X, m, n, p, r, s and t are defined above; and when $R^5$ is a protecting group, after the protecting group is removed, reacting a compound of the formula:

$$R^3\text{—L} \qquad (VI)$$

wherein L is a leaving group and $R^3$ is as defined in claim 1, therewith, or reductive conducting alkylation using a reducing agent and a compound of the formula:

$$R^6CHO \qquad (VII)$$

wherein $R^6$ is $C_{4-14}$ saturated or unsaturated aliphatic hydrocarbon; and optionally, wherein at least one of $R^1$ and $R^2$ is halogen, lower alkoxycarbonyl or aralkyloxycarbonyl, the halogen atom is reduced to a hydrogen atom, or in the case of lower alkoxycarbonyl or aralkyloxycarbonyl, it is converted to carbamoyl, lower alkylaminocarbonyl, di-lower alkylaminocarbonyl, lower alkoxycarbonyl(lower) alkylaminocarbonyl, aralkyloxycarbonyl(lower) alkylaminocarbonyl, aralkylaminocarbonyl, diaralkylaminocarbonyl or heteroaryl(lower)alkylaminocarbonyl, or both the reactions are carried out; and optionally further a compound of the formula:

$$R^4\text{—L} \qquad (X)$$

wherein $R^4$ is as defined in claim 1, and L is a leaving group, is reacted therewith.

8. A method of treating a disease or condition related to chemokine receptors in a mammal, which comprises administering an effective amount of one or more compounds of claim 1, to a mammal in need thereof.

9. The method of claim 8, wherein said disease is selected from the group consisting of acute inflammatory disease, chronic inflammatory disease, chronic inflammatory disease, acquired immune deficiency syndrome, ischemic reflux disorders, and arteriosclerosis.

10. The method of claim 9, wherein said chromic inflammatory disease is septicemia, pneumonia, or arthritis.

11. The method of claim 8, wherein said condition is an allergy or rejection symptoms after an organ transplantation operation.

12. A chemokine receptor antagonist composition, which comprises the compound of claim 1, or a pharmaceutically acceptable salt thereof, and a pharmaceutically acceptable carrier.

* * * * *